US012788732B2

(12) United States Patent
Wall

(10) Patent No.: US 12,788,732 B2
(45) Date of Patent: Nov. 10, 2026

(54) PRODRUG FOR THE TREATMENT OF DISEASE AND INJURY OF OXIDATIVE STRESS

(71) Applicant: Nacuity Pharmaceuticals, Inc., Fort Worth, TX (US)

(72) Inventor: G. Michael Wall, Fort Worth, TX (US)

(73) Assignee: Nacuity Pharmaceuticals, Inc., Fort Worth, TX (US)

( * ) Notice: Subject to any disclaimer, the term of this patent is extended or adjusted under 35 U.S.C. 154(b) by 304 days.

(21) Appl. No.: 17/156,560

(22) Filed: Jan. 23, 2021

(65) Prior Publication Data

US 2021/0228509 A1 Jul. 29, 2021

Related U.S. Application Data

(60) Provisional application No. 62/965,660, filed on Jan. 24, 2020.

(51) Int. Cl.

| | |
|---|---|
| ***A61K 31/16*** | (2006.01) |
| ***A61K 9/00*** | (2006.01) |
| ***A61P 27/02*** | (2006.01) |
| ***A61P 39/06*** | (2006.01) |

(52) U.S. Cl.

CPC ............ *A61K 31/16* (2013.01); *A61K 9/0051* (2013.01); *A61K 9/0053* (2013.01); *A61P 27/02* (2018.01); *A61P 39/06* (2018.01)

(58) Field of Classification Search

None

See application file for complete search history.

(56) References Cited

U.S. PATENT DOCUMENTS

| | | | |
|---|---|---|---|
| 1,114,369 | A | 10/1914 | Kukla |
| 3,340,147 | A | 9/1967 | Alexander et al. |
| 5,874,468 | A | 2/1999 | Atlas et al. |
| 6,420,429 | B1 | 7/2002 | Atlas et al. |
| 8,354,449 | B2 | 1/2013 | Goldstein |
| 8,937,099 | B2 | 1/2015 | Goldstein |
| 8,993,627 | B2 | 3/2015 | Goldstein |
| 9,216,162 | B2 | 12/2015 | Goldstein |
| 9,763,902 | B2 | 9/2017 | Warner et al. |
| 9,889,103 | B2 | 2/2018 | Warner et al. |
| 10,689,846 | B2 | 6/2020 | Ulette et al. |
| 11,052,018 | B2 | 7/2021 | Molnar |
| 11,092,017 | B2 | 8/2021 | Propheter-Hinckley |
| 2003/0027745 | A1 | 2/2003 | Repine |
| 2005/0112572 | A1 | 5/2005 | Pincemail et al. |
| 2009/0234011 | A1 | 9/2009 | Goldstein |
| 2012/0142550 | A1 | 6/2012 | Zehnder et al. |
| 2012/0150029 | A1 | 6/2012 | Debuc |
| 2013/0303436 | A1 | 11/2013 | Wilson |
| 2015/0164830 | A1 | 6/2015 | Goldsten |
| 2017/0020914 | A1 | 1/2017 | Castro Feo et al. |
| 2017/0333375 | A1 | 11/2017 | Campochiaro et al. |
| 2017/0370945 | A1 | 12/2017 | Campochiaro et al. |
| 2019/0135741 | A1 | 5/2019 | Wall |
| 2020/0281944 | A1 | 9/2020 | Piraee |
| 2021/0228509 | A1 | 7/2021 | Wall |

FOREIGN PATENT DOCUMENTS

| | | | |
|---|---|---|---|
| CA | 3078680 | A1 | 5/2019 |
| CA | 3079196 | C | 5/2021 |
| CN | 108618993 | A | 10/2018 |
| EP | 1975621 | A1 | 10/2008 |
| GB | 1114369 | A | 5/1968 |
| JP | 2005350405 | A | 12/2005 |
| JP | 2008538586 4 | A5 | 7/2009 |
| JP | 2013533234 | A | 8/2013 |
| JP | 2020-23549 | | 10/2018 |
| WO | 2003016527 | | 2/2003 |
| WO | 2004012652 | A2 | 2/2004 |
| WO | 2004028536 | A1 | 4/2004 |
| WO | 2006116353 | A2 | 11/2006 |
| WO | 2010048716 | A1 | 5/2010 |
| WO | 2011044230 | A2 | 4/2011 |

(Continued)

OTHER PUBLICATIONS

Li et al. (GLP-1 analogs containing disulfide bond exhibited prolonged half-life in vivo than GLP-1, Peptides, 2011 (Year: 2011).*

Kim et al. N-Acetylcysteine increase Corneal Endothelial Cell Survival in a Mouse Model for Fuchs Endothelial Corneal Dystrophy. Exp Eye Res. Oct. 2014; doi 10.1016/j.exer.2014.06.002 (Year: 2014).*

Maddirala et al. (Prevention and reversal of selenite-induced cataracts by N-acetylcysteine amide in Wistar rats, BMC Ophthalmology, 2017 (Year: 2017).*

Santus et al. (Oxidative Stress and Respiratory System: Pharmacological and Clinical Reappraisal of N-Acetylcysteine, COPD: Journal of Chronic Obstructive Pulmonary Disease, 2014) (Year: 2014).*

Amer, et al., "N-acetylcysteine amide (AD4) attenuates oxidative stress in beta-thalassemia blood cells." Biochimica et Biophysica Acta 1780 (2008) 249-255.

Australian Patent Office (ISA), International Search Report and Written Opinion for PCT/US2015/060172 Dated Apr. 13, 2016, 12 pg.

Australian Patent Office (ISA), International Search Report and Written Opinion for PCT/US2018/052065 dated Jan. 10, 2019, 10 pg.

(Continued)

*Primary Examiner* — Robert A Wax

*Assistant Examiner* — John Seungjai Kwon

(74) *Attorney, Agent, or Firm* — Edwin S. Flores; Daniel Chalker; Chalker Flores, LLP

(57) ABSTRACT

The present invention includes a method for using diNACA as a prodrug to deliver diNACA, NACA and NAC to a mammal for therapeutic purposes to prevent or treat diseases or disorders involving oxidative stress. The method includes any disease that involves the therapeutic use of NACA or NAC as a therapeutic agent. Also, compositions and methods for the prevention, reduction or treatment of corneal endothelial cell loss in a patient that comprise providing the patient with an amount of at least one, alone or in combination, of N-acetylcysteine amide (NACA) or (2R,2R')-3, 3'-disulfanediyl bis(2-acetamidopropanamide) (diNACA) (diNACA) to prevent or reduce the corneal endothelial cell loss or to prevent or treat presbyopia. DiNACA can be used to prevent or treat cataracts.

11 Claims, 6 Drawing Sheets

(56) References Cited

FOREIGN PATENT DOCUMENTS

| | | | | | |
|---|---|---|---|---|---|
| WO | 2013138744 | A1 | | 9/2013 | |
| WO | 2013163545 | A1 | | 10/2013 | |
| WO | 2014025792 | A1 | | 2/2014 | |
| WO | 2014100361 | A1 | | 6/2014 | |
| WO | 2015148880 | A1 | | 10/2015 | |
| WO | 2016073829 | A2 | | 5/2016 | |
| WO | WO 2016073931 | A1 | * | 5/2016 | |
| WO | 2017161318 | A1 | | 9/2017 | |
| WO | 2019060623 | A1 | | 3/2019 | |
| WO | 2019060634 | A1 | | 3/2019 | |
| WO | 2019060704 | A1 | | 3/2019 | |
| WO | 2019103915 | A1 | | 5/2019 | |
| WO | WO-2019094383 | A1 | * | 5/2019 | ............ A61K 31/00 |
| WO | WO-2019097434 | A1 | * | 5/2019 | ............ A61K 31/16 |
| WO | 2020102810 | A1 | | 5/2020 | |
| WO | 2020146660 | A1 | | 7/2020 | |
| WO | 2020146666 | A1 | | 7/2020 | |
| WO | 2020146674 | A1 | | 7/2020 | |
| WO | 2020146666 | A9 | | 9/2020 | |
| WO | 2021151044 | A1 | | 7/2021 | |

OTHER PUBLICATIONS

Australian Patent Office (ISA), International Search Report and Written Opinion for PCT/US2018/059446 dated Dec. 31, 2018, 15 pg.

Australian Patent Office (ISA), International Search Report and Written Opinion for PCT/US2018/061357 dated Dec. 18, 2018, 11 pg.

Australian Patent Office (ISA), International Search Report and Written Opinion for PCT/US2020/012968 dated Mar. 13, 2020, 10 pp.

Australian Patent Office (ISA), International Search Report and Written Opinion for PCT/US2020/012975 dated Mar. 13, 2020, 12 pp.

Australian Patent Office (ISA), International Search Report and Written Opinion for PCT/US2020/012983 dated Mar. 13, 2020, 15 pp.

Australian Patent Office, International Search Report and Written Opinion PCT/US2021/014819 dated Mar. 25, 2021, 18 pp.

Australian Patent Office, International Search Report and Written Opinion PCT/US2021/036210 dated Jul. 19, 2021, 12 pp.

Australian Patent Office, Examination Report for Australian Appl. No. 2020227015 dated Sep. 24, 2021, 6 pp.

Babizhayev, et al., Revival of the Lens Transparency with N-Acetylcarnosine.: Current Drug Therapy, 2006:1; 91-116.

Bean, et al., "Comparative evaluation of antioxidant reactivity within obstructed and control rabbit urinary bladder tissue using FRAP and CUPRAC assays," Molecular and Cellular Biochemistry (2008) 323(1-2):139-142.

Bernardes, et al., "From Disulfide- to Thioether-Linked Glycoproteins" Angewandte Chemie, Supporting Information (2008), S1-S97.

Boone, Kevin "The K-Zone: Biophysical Data Tables", 1994-2006, downloaded from www.kevinboone.com on Mar. 14, 2009.

Buss, et al., "Protein carbonyl measurement by a sensitive ELISA method." Free Radic Biol Med, (1997), 23(3):361-6.

Campochiaro, et al., "Oral N-acetylcysteine improves cone function in retinitis pigmentosa patients in phase I trial." J Clin Invest. 2020 130(3):1527-1541.

Campochiaro, et al. "Is there Excess Oxidative Stress and Damage in Eyes of Patients with Retinitis Pigmentosa" Antioxidants Redox Signaling, (2015) 23(7):643-648.

Campochiaro, et al. "The Mechanism of Cone Cell Death in Retinitis Pigmentosa", Progress in Retinal and Eye Research (2018), 62:24-37.

Carey, et al., "In vivo inhibition of I-buthionine-(S, R)-sulfoximine-induced cataracts by a novel antioxidant, N-acetylcysteine amide." Free Radical Biol Med. 2011;15.

Carey, et al. "N-acetyl-L-cysteine amide protects retinal pigment epithelium against methamphetamine-induced oxidative stress" Journal of Biophysical Chemistry, vol. 3, No. 2, 101-110 (2012).

Carroll, et al., "Simultaneous quantitation of oxidized and reduced glutathione via LC-MS/MS: An insight into the redox state of hematopoietic stem cells." Free Radical Biology and Medicine, 97 (2016) 85-94.

Celma, et al., "Determination of N-acetylcysteine in human plasma by liquid chromatography coupled to tandem mass spectrometry." J Chrom A, 870 (2000) 13-22.

Chastain, et al. "Distribution of topical ocular nepafenac and its active metabolite amfenac to the posterior segment of the eye." Exp Eye Res (2016), 145:58-67.

Davies, et al., "Measurements of protein carbonyls, ortho- and meta-tyrosine and oxidative phosphorylation complex activity in mitochondria from young and old rats." Free Radic Biol Med, (2001), 31(2):181-90.

Devries, et al. "N-acetyl-l-cysteine." J Cell Biochem Suppl (1993), 17F:270-277.

Dietz, et al., "Photochemical Reduction of 5-Bromouracil by Cysteine Derivatives and Coupling of 5-Bromouracil to Cystine Derivatives," Photochemistry and Photobiology (1989), 49(2):121-129.

Dietzsch, et al., "Cystic fibrosis: comparison of two mucolytic drugs for inhalation treatment (acetylcysteine and arginine hydrochloride)." Pediatrics 1975;55:96-100.

Dong, et al., "Compared with N-acetylcysteine (NAC), N-Acetylcysteinne Amid (NACA) Provides Increased Protein of Cone Function in a Model of Retinitis Pigmentosa." Investigative Ophthalmology Visual Science, (2014), 55:1-2. (Abstract).

Ehre, et al. An Improved Inhaled Mucolytic to Treat Airway Muco-obstructive Diseases. Am J Respir Crit Care Med. Jan. 15, 2019;199(2):171-180. doi: 10.1164/rccm.201802-0245OC.

Ercal, et al., "Effects of a thiol antioxidant in various cataract models," Acta Ophthalmologica (2016), 94:S256 (Abstract).

Ercal, et al., High-performance liquid chromatography assay for N-acetylcysteine in biological samples following derivatization with N-(1-pyrenyl)maleimide. J Chrom B, 685 (1996) 329-334.

European Patent Office, Extended European Search Report for 15770142.6 dated Oct. 20, 2017.

European Patent Office, Extended European Search Report for EP 15857309.7 dated May 23, 2018.

European Patent Office, Extended European Search Report for 15858590.1 dated May 2, 2018.

European Patent Office, Extended European Search Report for EP 18876329.6 dated Oct. 29, 2019.

European Patent Office, Extended European Search Report for EP 18882212.6 dated Jul. 6, 2021, 8 pp.

Giustarini, et al., Pitfalls in the analysis of the physiological antioxidant glutathione (GSH) and its disulfide (GSSG) in biological samples: an elephant in the room. J Chrom B., 1019 (2016) 21-28.

Han, et al., "Efficacy of nebulized acetylcysteine for relieving symptoms and reducing usage of expectorants in patients with radiation pneumonitis." Thoracic Cancer 2018; 1-6. doi: 10.1111/1759-7714.12938.

Heymann, et al., "The preparation and Some Biological Properties of the Asperagine Analog L-2@-Amino-2-carboxyethanesulfonamide," J Am Chem Soc (1959), 81(19):5125-5128.

Intellectual Property India, First Examination Report for Indian Appl. No. 201917036550 dated Sep. 22, 2021, 7 pp.

Jastrzębska, et al., "N-acetylcysteine amide (AD4) reduces cocaine-induced reinstatement." Psychopharmacology 2016;33:3437-3448.

Jones, "Extracellular Redox State: Refining the Definition of Oxidative Stress in Aging," Rejuvenation Research (2006), 9(2):169-181.

Kahns, et al., "Prodrugs as drug delivery systems. 107. Synthesis and chemical and enzymatic hydrolysis kinetics of various mono- and diester prodrug of N-acetylcysteine." Int J Pharm (1990), 62:193-205.

Katz, et al., Cerebrospinal fluid concentrations of N-acetylcysteine after oral administration in Parkinsons disease. Parkinsonism and Related Disorders, 21 (2015) 500-503.

(56) References Cited

OTHER PUBLICATIONS

Kelly, "Clinical applications of N-acetylcysteine." Altern Med Rev J Clin Ther. (1998), 3(2):114-27.
Kim, et al., "N-Acetylcysteine increases corneal cell survival in a mouse model of Fuchs endothelial corneal dystrophy," Experimental Eye Research (2014), 127:20-25.
Komeima, et al., "Antioxidants reduce cone cell death in a model of retinitis pigmentosa." PNAS, (2006), 103 (30):11300-11305.
Komeina, et al., "Antioxidants slow photoreceptor cell death in mouse models of retinitis pigmentosa." J Cell Physiol. (2007), 213(3):809-15.
Komeina, et al., "Blockade of neuronal nitric oxide synthase reduces cone cell death in a model of retinitis pigmentosa." Free Radic Biol Med, (2008), 45(6):905-12.
Bahat-Stroomza, et al. "A novel thiol antioxidant that crosses the blood brain barrier protects dopaminergic neurons in experimental models of Parkinson's disease" European Journal of Neuroscience, 2005; 21: 637-646.
Banerjee, et al. HIV proteins (gp120 and Tat) and methamphetamine in oxidative stress-induced damage in the brain: Potential role of the thiol antioxidant N-acetylcysteine amide. Free Radic Biol Med. May 15, 2010; 48(10): 1388-1398.
Carey, et al. "In vivo inhibition of I-buthionine-(S, R)-sulfoximine-induced cataracts by a novel antioxidant, N-acetylcysteine amide" Free Radical Biol Med. 2011;15, Available online Dec 21, 2010.
Ercal, et al., "Effects of a thiol antioxidant in various cataract models," Acta Ophthalmologica (Sep. 2016), 94:S256 (Abstract only).
Wang, et al. "Hyperoxia-induced lens damage in rabbit: protective effects of N-acetylcysteine" Mol Vis. 2009;15:2945-52, Published Dec. 31, 2009.
Zhang, et al. "Effects of N-acetylcysteine and glutathione ethyl ester drops on streptozotocin-induced diabetic cataract in rats" Mol Vis. 2008; 14:862-70, Published May 12, 2008.
Australian Patent Office, International Search Report and Written Opinion PCT/US2021/014819 dated Mar. 25, 2021.
Dong, et al., "Compared with N-acetylcysteine (NAC), N-Acetylcysteine Amide (NACA) Provides Increased Protection of Cone Function in a Model of Retinitis Pigmentosa", Investigative Ophthalmology & Visual Science, 2014, vol. 55, iss. 13, p. 1736, <URL: https://iovs.arvojournals.org/article.aspx?articleid=2267004>.
Kusmierek, et al., Ultraviolet derivatization of low-molecular-mass thiols for high performance liquid chromatography and capillary electrophoresis analysis, J Chrom B, 879 (2011) 1290-1307.
Grinberg, et al., "N-acetylcysteine amide, a novel cell-permeating thiol, restores cellular glutathione and protects human red blood cells from oxidative stress," Free Radical Biol Med. (2005) ;38(1):136-145.
Lee, et al., "N-Acetylcysteine Promotes Long-Term Survival of Cones in a Model of Retinitis Pigmentosa," J Cell Physiol (2011), 226:1843-1849, published online Nov. 10, 2010 Levine, R.L., "Carbonyl modified proteins in cellular regulation, aging, and disease" Free Radic Biol Med, 2002. 32(9): p. 790-6.
Li, et al, "A Convenient Synthesis of Amino Acid Methyl Esters", Molecules (2008), 13:1111-1119.
Liu, et al., "A rabbit model to study biochemical damage to the lens after vitrectomy: effects of N-acetylcysteine." Exp Eye Res. 2009;88(6):1165-70.
Lu, et al., "Effects of Different Types of Oxidative Stress in RPE Cells," J Cell Phys (2006), 206(1):119-125.
Maddirala, et al. "Prevention and reversal of selenite-induced cataracts by N-acetylcysteine amide in Wistar rats" BMC Ophthalmology (2017) 17:54.
Martin, Tellis, "Amides of N-Acylcysteines as Mucolytic Agents", J Med Chem (1967), 10:1172-1176.
Martinez-Fernandez De La Camara, et al., Altered Antioxidant-Oxidant Status in Aqueous Humor and Peripheral Blood of Patents with Retinitis Pigmentosa, PLOS ONE (2013), 8(9):E74223.
McMenamim, et al., Simultaneous analysis of multiple aminothiols in human plasma by high performance liquid chromatography with fluorescence detection, J Chrom B, 877 (2009) 3274-3281.
Minozzi et al., "An Insight into the Radical Thiol/Yne Coupling: The Emergence of Arylalkyne-tagged Suggars for te Direct Photoinduced Glycosylation of Cysteine Containing Peptides", J. Org. Chem, 2011, 76, 450-459.
Miller, WF. "Aerosol therapy in acute and chronic respiratory disease." Arch Intern Med 1973;131:148-155.
Monostori, et al., Determination of glutathione and glutathione disulfide in biological samples: an in-depth review. J Chrom B, 877 (2009) 3331-3346.
Moore, et al., A new LC-MS/MS method for the clinical determination of reduced and oxidized glutathione from whole blood. J Chrom B, 929 (2013) 51-55.
Nakagami, et al. "A novel Nrf2 activator from microbial transformation inhibits radiation-induced dermatitis in mice," Journal of Radiation Research, vol. 57, No. 5, 2016, pp. 567-571.
Nash, et al., "Nebulized and oral thiol derivatives for pulmonary disease in cystic fibrosis." Cochrane Database Syst Rev 2009;(1):CD007168.
New, et al., Evaluation of BEH C18, BEH HILIC, and HSS T3 (C18) Column Chemistries for the UPLC-MS-MS Analysis of Glutathione, Glutathione Disulfide, and Ophthalmic Acid in Mouse Liver and Human Plasma. J Chrom Sci, 46 (2008) 209-214.
Niemeyer, Selective Rod-and Cone-ERG Responses on Retinal Degenerations, Digital Journal of Ophthalmology, 1998, vol. 4, No. 10, 1998.
Nozal, et al., Determination of glutathione, cysteine, and N-acetylcysteine in rabbit eye tissues using high-performance liquid chromatography and post-column derivatization with 5,5'-dithiobis(2-nitrobenzoic acid). J Chrom A, 778 (1997) 347-353.
Park, et al.: "Targeted and Reversible Blood-Retinal Barrier Disruption via Focused Ultrasound and Microbubbles" PLoS ONE (2012), 7(8):e42754.
Poole, et al., "Mucolytic agents versus placebo for chronic bronchitis or chronic obstructive pulmonary disease." Cochrane Database Syst Rev 2015;(7):CD001287).
Reyes, et al., Neuronal glutathione content and antioxidant capacity can be normalized in situ by N-acetyl cysteine concentrations attained in human cerebrospinal fluid, Neurotherapeutics, 13 (2016) 217-225.
Riley, et al., "Glutathione in the aqueous humor of human and other species." Investigative ophthalmology & visual science, (1980), 9(1):94-96.
Rubin BK. "Aerosol Medications for Treatment of Mucus Clearance Disorders Respiratory care" 2015; 60(6): 825-832.
Šalamon, et al., "Medical and Dietary Uses of N-Acetylcysteine." Antioxidants 2019, 8, 111.
Sekhon, "Exploiting the Poer of Stereochemistry in Drugs . . . ", Journal of Modern Medicinal Chemistry, 2013, 10-36.
Shen, et al., "Oxidative damage is a potential cause of cone cell death in retinitis pigmentosa." J Cell Physiol, (2005), 203(3):457-64.
Shen, et al., "Oxidative damage in age-related macular degeneration," Histology and Histopathology (2007), 22 (12):1301-1308.
Shintani, et al., "Review and Update: Current treatment trends for Patients with Retinitis Pigmentosa," Optometry (2009), 80:384-401.
SUPELCO "Methanolic H2S04 (10./o v/v)" 1997, Sigma-Aldrich Co., 2 Pages.
Squellerio, et al., Direct glutathione quantification in human blood by LC-MS/MS: comparison with HPLC with electrochemical detection. J Pharm Biomed Anal, 71 (2012) 111-8.
Stey, et al., "The effect of oral N-acetylcysteine in chronic bronchitis: a quantitative systematic review." Eur Respir J. 2000; 16(2):253-62.
Suh, et al., Clinical assay of four thiol amino acid redox couples by LC-MS/MS: utility in thalassemia, J Chrom B, 877 (2009) 3418-3427.
Sunitha, et al., N-acetylcysteine amide: a derivative to fulfull the promises of N-acetylcysteine. Free Radic Res, 47 (2013) 357-367.

(56) References Cited

OTHER PUBLICATIONS

Tam, et al., "Nebulized and oral thiol derivatives for pulmonary disease in cystic fibrosis." Cochrane Database Syst Rev 2013;(7):CD007168.
Tarrant et al. "Mucoactive agents for adults with acute lung conditions: A systematic review." Heart & Lung (2019) 48 (2):141-147.
Tobwala et al. "N-acetylcysteine Amide (NACA), a Novel GSH Prodrug: Its Metabolism and Implications in Health", Labrou, 2013, Capter VI. ISBN:978-1-62417-460-5.
Tse, et al., "High-dose N-acetylcysteinine in stable COPD: the 1-year, double-blind, randomized, placebo-controlled HIACE study." Chest, (2013). 144(1):106-118.
Tuson, et al., "Overexpression of CERKL, a gene responsible for retinitis pigmentosa in humans, protects cells from apoptosis induced by oxidative stress." Mol Vis. (2009), 15:168-80.
United States Patent & Trademark Office (ISA) International Search Report and Written Opinion PCT/US2015/059589 Dated Feb. 2, 2016, 10 pg.
University of Sao Paulo, et al. "N-Acetyl Cysteine for Cystinosis Patients", ClinicalTrials.gov [online], identifier: NCT01614431, Last update posted: Jun. 20, 2012, https://clinicaltrials.gov/ct2/show/NCT01614431, [retrieved online Jul. 9, 2021].
Usui, et al., "Overexpression of SOD in retina: Need for increase in H202-detoxifying enzyme in same cellular compartment," Free Radical Biology and Medicine (2011 ), 51(7): 1347-1354.
Usui, et al., "Increased expression of catalase and superoxide dismutase 2 reduces cone cell death in retinitis pigmentosa." Mol Ther J Am Soc Gene Ther. (2009), 17(5):778-86.
Usui, et al., "NADPH oxidase plays a central role in cone cell death in retinitis pigmentosa." J Neurochem. (2009), 110(3):1028-37.
Wang, et al., "Relationship of protein-glutathione mixed disulfide and thioltransferase in H202-induced cataract in cultured pig lens." Exp Eye Res. May 1997;64(5):693-700.
Wang, et al., "Hyperoxia-induced lens damage in rabbit: protective effects of N-acetylcysteine." Mol Vis. 2009; 15:2945-52.
Weng, Bioanalytical liquid chromatography tandem mass spectrometry methods on underivatized silica columns with aqueous/organic mobile phases. J Chrom B, 796 (2003) 209-224.
Wu, et al., "Effects of N-acetylcysteine amide (NACA, a thiol antioxidant on radiation-induced cytotoxicity in Chenese hamster ovary cells," Life Sciences (2008), 82:1122-1130.
Wu, et al., Separation and quantification of N-acetyl-L-cysteine and N-acetyl cysteine-amide by HPLC with fluorescence detection. Biomed Chromatogr, 20 (2006) 415-422.
Yu, et al., "Intraretinal oxygen levels before and after photoreceptor loss in the RCS rat." Invest Ophthalmol Vis Sci, (2000), 41(12):3999-4006.
Adil, et al. "N-acetylcysteine in dermatology" Indian Journal of Dermatology, Feb. 2018.
Canadian Patent Office, Examination Report for Appl. No. 3,046,363 dated Jun. 6, 2022, 4 pp.
Cherqui, et al. "The renal Fanconi syndrome in cystinosis: pathogenic insights and therapeutic perspectives" Nal Rev Nephrol. Feb. 2017: 13(2): 115-131.
Demirel, et al. "The preventive effect of N-acetylcysteine on radiation-induced dermatitis in a rat model" Journal of BUON, 15:577-582, 2010.
Elmonem, et al. "Cystinosis: a review" Orphanet Journal of Rare Diseases (2016) 11:47.
European Patent Office, Extended European Search Report for EP 20738980.0 dated Jan. 28, 2022, 9 pp.
European Patent Office, Extended European Search Report for EP 20738196.3 dated Sep. 22, 2022, 12 pp.
European Office Action, Examination Report for EP Patent Appl No. 21217485.8 dated Nov. 20, 2023, 5 pp.
Hong, et al. "Effect of High-Dose Intravenous N-acetylcysteine on the Concentration of Plasma Sulfur-Containing Amino Acids", The Korean Journal of Internal Medicine: 20:217-223, 2005.
Hsu, et al. "Feasibility of corneal drug delivery of cysteamine using vitamin E modified silicone hydrogel contact lenses" European Journal of Pharmaceutics and Biopharn1aceutics 85 (2013) 531-540.
Japan Patent Office, Notification of Reasons for Refusal dated Dec. 18, 2023 for Japanese Appl. No 2021-540019 (with english translation), 8 pp.
Katz, et al. "Contrast Sensitivity Function in Nephropathic Cystinosis", Arch Ophthalmol vol. 105, 1987).
Kunisada, et al. "CXCL1 Inhibition Regulates UVB-Induced Skin Inflammation and Tumorigenesis in Xpa-Deficient Mice" Journal of Investigative Dermatology (2017), 137, 1975-1983.
Offen, et al. "A low molecular weight copper chelator crosses the blood-brain barrier and attentuates experimental autoimmune encephalomyelitis" Journal of Neurochemistry, 2004, 89, 1241-1251.
Reagan-Shaw, et al. "Dose translation from animal to human studies revised" The FASEB Journal, Mar. 2007, vol. 22, (659-661).
Shams, et al. "Treatment of corneal cystine crystal accumulation in patients with cystinosis" Clinical Opthamalogy, Oct. 10, 2014, 2077-2078.
Sunitha, et al. "N-Acetylcysteine amide: a derivative to fulfill the promises of N-Aceylcysteine" Free Radical Resarch, May 2013, 47(5), 357-367.
Tsai, et al. "Topical TV-Acetylcysteine Accelerates Wound Healing in Vitro and in Vivo via the PKC/Stat3 Pathway" Int. J. Mol. Sci., 2014, 15, 7563-7578.
Vaisbich, et al. "Oxidative Stress in Cystinosis Patients" Nephron Extra, 2011; 1:73-77, publishes online Sep. 19, 2011.
Yigit, et al. "Release of N-acetylcysteine and N-ACETYLCYSTEINE Amide from Contact Lenses" Eye Contact Lens, vol. 39, No. 5, Sep. 2013.

* cited by examiner diNACA

NACA

NAC

PRODRUG FOR THE TREATMENT OF DISEASE AND INJURY OF OXIDATIVE STRESS

CROSS-REFERENCE TO RELATED APPLICATIONS

This application claims priority to U.S. Provisional Application Ser. No. 62/965,660, filed Jan. 24, 2020, the entire contents of which are incorporated herein by reference.

STATEMENT OF FEDERALLY FUNDED RESEARCH

Not applicable.

TECHNICAL FIELD OF THE INVENTION

The present invention relates in general to the use of (2R,2R')-3,3'-disulfanediyl bis(2-acetamidopropanamide) (diNACA) as a prodrug to NACA and NAC for the prevention and/or treatment of various diseases and/or disorders involving oxidative stress.

BACKGROUND OF THE INVENTION

Antioxidants, NAC or NACA, have many uses and potential uses for the treatment of numerous diseases and disorders involving oxidative stress by virtue of their antioxidant, anti-apoptotic, anti-inflammatory and neuroprotective properties (Šalamon S, Kramar B, Marolt T P, Poljšak B, Milisav I.; Medical and Dietary Uses of N-Acetylcysteine. Antioxidants 2019, 8, 111; doi:10.3390/antiox8050111; Sunitha K, Hemshekhar M, Thushara R, Santhosh M S, Yariswamy M, Kemparaju K, et al. N-acetylcysteine amide: a derivative to fulfill the promises of N-acetylcysteine. Free Radical Res 2013; 47:357-367). A few of these uses are described in below.

Mucolysis. U.S. Pat. No. 3,340,147 claims the use of NAC as a mucolytic. NAC was approved by United States Food and Drug Administration (FDA) for use as a mucolytic (MUCOMYST®).

Hepatotoxicity. NAC was approved by FDA for use in the treatment of hepatotoxicity caused by acetaminophen overdose ACETADOTE®, and CETYLEV®.

U.S. Pat. No. 9,216,162B2 claims the use of NACA for blocking or reducing hepatic toxicity of acetaminophen. However, it does not teach the use of diNACA as a prodrug to NACA or NAC for blocking or reducing hepatic toxicity of acetaminophen.

U.S. patent application Ser. No. 14/632,089 (publication number US20150164830A1) claims the use of NACA for blocking or reducing hepatic toxicity of acetaminophen. However, it does not teach the use of diNACA as a prodrug to NACA or NAC for blocking or reducing hepatic toxicity of acetaminophen.

Ophthalmological Use. NACA for Retinal Disease and Disorders.

Schimel et al. (Schimel A M, Abraham L, Cox D, Sene A, Kraus C, Dace D S, et al. N-acetylcysteine amide (NACA) prevents retinal degeneration by up-regulating reduced glutathione production and reversing lipid peroxidation. Am J Pathol 2011; 178:2032-2043.) showed that treatment of human retinal pigment epithelial cells with NACA protected against oxidative stress-induced cellular injury and death.

Retinitis Pigmentosa. NAC for Retinitis Pigmentosa (RP). Oral high dose NAC improved visual acuity (2-5 letters;

$p<0.05$) and increased aqueous humor concentrations of NAC in RP patients ($n=30$) (Campochiaro P A, Iftikhar M, Hafiz G, Akhlaq A, Tsai G, Wehling D, Lu L, Wall G M, Singh M S, Kong X. Oral N-acetylcysteine improves cone function in retinitis pigmentosa patients in phase I trial. J Clin Invest. 2020. https://doi.org/10.11172/JCI132990).

NACA for Retinitis Pigmentosa. U.S. patent application Ser. No. 15/523,665 teaches the use of NACA for the treatment of RP. NACA has been shown to improve, to a greater extent than NAC, visual parameters in a mouse model of RP.

Corneal Endothelial Cell Survival. NAC increased corneal endothelial survival in a cell culture and mouse model (Kim E C, Meng H; Jun A S. N-Acetylcysteine Increases Corneal Endothelial Cell Survival in a Mouse Model of Fuchs Endothelial Corneal Dystrophy. Exp Eye Res 2014; 127: 20-25.).

Cataract. NAC has shown activity in protecting the eye lens against oxidative-induced cataracts, preventing post-vitrectomy cataracts, or inhibiting the progression of diabetic cataract at the earlier stage. (Wang P, Liu X C, Yan H, Li M Y. Hyperoxia-induced lens damage in rabbit: protective effects of N-acetylcysteine. Mol Vis. 2009; 15:2945-52; Liu X C, Wang P, Yan H. A rabbit model to study biochemical damage to the lens after vitrectomy: effects of N-acetylcysteine. Exp Eye Res. 2009; 88(6):1165-70. doi: 10.1016/j.exer.2009.01.001.; Zhang S, Chai F Y, Yan H, Guo Y, Harding J, Effects of N-acetylcysteine and glutathione ethyl ester drops on streptozotocin-induced diabetic cataract in rats. Mol Vis. 2008; 14:862-70.)

NACA has been shown to inhibit sodium selenite-induced and 1-buthionine-(S,R)-induced cataracts (Maddirala et al. BMC Ophthalmology (2017) 17:54; and Carey J W, Pinarci E Y, Penugonda S, Karacal H, Ercal N. In vivo inhibition of I-buthionine-(S,R)-sulfoximine-induced cataracts by a novel antioxidant, N-acetylcysteine amide. Free Radical Biol Med. 2011; 15; 50(6):722-9. doi: 10.1016/j.Free Rad Biol Med.2010.12.017, respectively).

Patent Publication WO2013/163545A1 is said to teach a method of treating cataracts using a therapeutically effective amount of NACA. However, WO2013/163545A1 does not describe the use of NACA to prevent or delay the formation of cataracts. Further, WO2013/163545A1 does not describe the use of diNACA as a prodrug to deliver NACA to the eye for the treatment or prevention of cataracts.

Patent Publications US20200281944A1, PCT/IB2018/058979 and CA3078680 relate to the use of NAC esterified with lanosterol or 25-hydroxycholesterol for the treatment of lens disorders and using lanosterol or 25-hydroxycholesterol derivatives in combination with NAC or NACA for the treatment of lens disorders. However, they do not teach the use of NAC alone or NACA alone for the prevention or treatment of cataract or the use of diNACA as a prodrug to deliver NACA or NAC to the eye for the prevention or treatment of cataract, or any other indication.

Presbyopia. Patent Publications US20200281944A1, PCT/IB2018/058979 and CA3078680 are said to teach the use of NAC esterified with lanosterol or 25-hydroxycholesterol for the treatment of lens disorders using lanosterol or 25-hydroxycholesterol derivatives in combination with NAC or NACA for the treatment of lens disorders. However, they fail to teach the use of NAC alone or NACA alone for the prevention or treatment of presbyopia or the use of diNACA as a prodrug to deliver NACA or NAC to the eye for the prevention or treatment of presbyopia, or any other indication.

Skin hyperpigmentation or skin rejuvenation. Melanin, the primary component of skin pigmentation secreted by melanocytes, protects the skin from harmful ultraviolet (UV) radiation, however, accumulation of melanin pigment in sun-damaged skin results in various hyperpigmentation disorders. Antioxidants, NACA ("NPI-001") and diNACA ("NPI-002"), inhibited melanin production in human melanocytes and increased glutathione and NAC in healthy human skin explants exposed to UV-radiation. Taken together, these findings support the theory that reactive oxygen species are involved in melanogenesis in reconstructed human epithelium cultures as well as skin exposure to UV irradiation. Glutathione (GSH) inhibits melanogenesis by suppressing the activity of tyrosinase, and oral administration of GSH in humans reduces melanin production in the skin. Indeed, significant inhibition of tyrosinase activity was observed in a dose responsive manner with NACA and diNACA. Based on these results, NACA and diNACA have therapeutic utility as antioxidants, i.e., potential therapeutics for skin (Neil J; Wall G M; Brown M. Antioxidant Effects of N-acetylcysteine Amide and NPI-002 on Human Skin or Equivalents. AAPS PharmSci360, Poster Abstract, Oct. 26-Nov. 5, 2020).

Concussion. U.S. Pat. No. 8,993,627B2 is said to teach the use of NACA delivered in various forms and concentrations by various routes for prevention or treatment of concussion. However, it fails to use or teach diNACA administered in any form or route as a prodrug to NACA or NAC for preventing or treating concussion.

Ionizing Radiation. U.S. Pat. No. 8,937,099B2 claims the use of NACA delivered in various forms and concentrations by various routes for prevention or treatment of exposure to ionizing radiation. However, it fails to teach use of diNACA administered in any form or route as a prodrug to NACA or NAC for preventing or treating exposure to ionizing radiation.

Traumatic brain Injury or Spinal Cord injury Resulting from a High Energy Blast. U.S. Pat. No. 8,354,449B2 is said to teach NACA delivered in various forms and concentrations by various routes for treatment of traumatic brain injury or spinal cord injury resulting from exposure to a high-energy impulse blast. However, it fails to teach the use of diNACA administered in any form or route as a prodrug to NACA or NAC for treatment of traumatic brain injury or spinal cord injury resulting from exposure to a high-energy impulse blast.

Macular Degeneration. U.S. patent application Ser. No. 15/943,236 claims the use of NACA delivered in various forms and concentrations by ophthalmic route for treatment of macular degeneration. However, it fails to teach the use of diNACA administered in any form or route as a prodrug to NACA or NAC for treatment of macular degeneration.

Other Antioxidants for Ophthalmology. Lipoic Acid Choline Ester for Presbyopia. Presbyopia is the result of several ophthalmic changes. The crystalline lens enlarges over time, the ciliary body undergoes atrophic changes, the vitreous becomes less viscous, and the lens loses its flexibility. With age, proteins called crystallins in our natural lenses begin to cross-link, causing loss in plasticity of the lens. Initially, this manifests as loss of accommodation and thereby decreasing ability to focus on near objects, and eventually, opacity, or cataract. Therefore, presbyopia and cataract are thought to be a continuum of the antioxidant processes ongoing in the natural lens as we age. This process may be accelerated by therapeutic agents (e.g., topical corticosteroid eye drops), surgery (e.g., vitrectomy), or other causes. Antioxidants have shown some efficacy in the treatment of presbyopia and cataract.

A recent study has demonstrated that topical ocular antioxidant therapy may treat presbyopia. EV06 ophthalmic solution (lipoic acid choline ester, LACE) 1.5% eyedrops (Encore Vision), dubbed UNR844 by Novartis, is a prodrug used to deliver lipoic acid to the lens (https://www.eyeworld.org/has-presbyopia-found-encore). LACE penetrates the cornea and is metabolized into choline and lipoic acid, two naturally occurring substances. Enzymes within lens fiber cells chemically reduce lipoic acid to active form dihydrolipoic acid (DH-LA). DHLA purportedly reduces disulfide bonds between lens proteins and restores lens microfluidics by increasing the deformability of the crystalline lens and increasing the accommodative amplitude.

The hypothesis that drove the development of LACE addressed lens flexibility or the lack thereof in presbyopia. As lens proteins oxidize over time, disulfide bonds form, rendering them less able to move relative to one another during the act of accommodation. The hypothesis was that topical application of an antioxidant agent, LACE, could disrupt the cross-linked disulfide bonds, the proteins would regain increased flexibility and allow a greater range of deformation of the lens, thereby translating into a greater dynamic range of accommodation. LACE facilitated ocular delivery of DHLA to the lens. Once within the lens, DHLA purportedly reduced disulfide bonds between lens proteins and restored lens microfluidics. Proof of concept was first confirmed in vitro with human cadaver lenses and in vivo in rabbit eyes, whereby the drug produced lens softening and an increase in lens deformability (https://www.eyeworld.org/has-presbyopia-found-encore).

A small first-in-human clinical trial of LACE in presbyopes showed that the drug was relatively safe, robust, and persistent, even after the regimen was stopped, demonstrating statistically significant near visual acuity (distance corrected near visual acuity (DCNVA)) improvement compared to placebo.

The clinical study was a prospective, randomized, double-masked, placebo-controlled study including 75 patients (45-55 years) with hyperopia, myopia, or emmetropia and a diagnosis of presbyopia, from four U.S. sites. Patients were randomized 2:1 (EV06=50:placebo:=25). The investigational product was given for 91 days and patients were monitored during a 7-month follow-up period. At baseline, study patients had DCNVA below 20/40 in each eye, best corrected distance visual acuity (BCDVA) of 20/20 or better in each eye, and a difference of ≤0.50 D between manifest refraction spherical equivalent and cycloplegic refraction spherical equivalent.

Visual acuity improvements were most pronounced when subjects employed bilateral vision, with 84% achieving 20/40 bilateral vision or better versus 52% in the placebo group. Fifty-three percent of the study participants achieved a ~0.2 log MAR change in the bilateral vision versus 22% in placebo. No subjects discontinued, and there were no sight threatening AEs or changes in IOP. The drug was comfortable upon installation and caused no change in best corrected distance visual acuity, manifest refraction spherical equivalent, cycloplegic refraction, or in pupil diameter. The drug effects on near visual improvement persisted in the study group long after dosing with EV06 was stopped at day 91. Significant effects were reported compared to placebo 241 days after the end of the study period, with only a small amount of treatment degradation. "Seven months after the end of the 3-month study time, 39% of the subjects treated maintained a ≥0.2 log MAR change in bilateral near vision, compared to only 6% in placebo (www.eyeworld.org/has-presbyopia-found-encore).

N-Acetylcarnosine for Cataracts. Studies have demonstrated that topical ocular antioxidant therapy may prevent and/or treat cataracts. Free-radical-induced lipid oxidation (LPO) as a mechanism in the development of cataracts has been reported (Babizhayev M A, Deyev A I, Yermakova V N, Remenshchikov V V, Bours J. Revival of the Lens Transparency with N-Acetylcarnosine. Current Drug Therapy, 2006:1; 91-116). Initial stages of cataract are characterized by the accumulation of primary (diene conjugates, cetodienes) LPO products, while in later stages there is a prevalence of LPO fluorescent end products. Increase in fatty acyl content of lenticular lipids was shown by gas chromatographic analysis producing fatty acid fluoro-substituted derivatives. Lens opacity degree correlates with the level of the LPO fluorescent end product accumulation in lens accompanied by thiol (—SH) group oxidation of lens proteins due to a decrease of reduced glutathione (GSH) concentration in the lens. Injection of LPO products into the vitreous humor was shown to induce cataract. Peroxide damage of the lens fiber membranes may be the initial cause of cataract formation. Babizhayev et al. (2006) developed eye drops containing N-acetylcarnosine suitable for the non-surgical prevention and treatment of age-related cataracts. The N-acetylcarnosine eyedrops protected the crystalline lens from oxidative stress-induced damages and in a clinical trial produced a long-term improvement in sight. When administered topically to the eye, N-acetylcarnosine eyedrops delivered L-carnosine to the aqueous humor. The effects of N-acetylcarnosine eyedrops on lens opacities were examined in patients with cataracts and canines with age-related cataracts. The positive effect on lens clarity and clarifying modification of opacification zones was demonstrated. These results suggested a positive effect of treatment (both reversal and prevention) of age-related cataracts by a topical antioxidant, N-acetylcarnosine eye drops. (WO 2004/028536 A1).

Neurogenerative Diseases and Substance Abuse. Parkinson's disease (PD). A study has demonstrated that NACA penetrates the brain and protects neurons in general and especially dopaminergic cells against various oxidative stress-generating neurotoxins in tissue cultures. Treatment with NACA markedly decreased the damage of dopaminergic neurons in three experimental models of PD. NACA suppressed amphetamine-induced rotational behaviour in rats with unilateral 6-OHDA-induced nigral lesion. It attenuated the reduction in striatal dopamine levels in mice treated with 1-methyl-4-phenyl-1,2,3,6,-tetrahydropyridine. It also reduced dopaminergic neuronal loss following chronic intrajugular administration of rotenone in rats. Therefore, NACA may be effective at slowing down nigral neuronal degeneration and illness progression in patients with PD (Bahat-Stroomza M, Gilgun-Sherki Y, Offen D, Panet H, Saada A, Krool-Galron N, Barzilai A, Atlas), Melamed E A novel thiol antioxidant that crosses the blood brain barrier protects dopaminergic neurons in experimental models of Parkinson's disease. European Journal of Neuroscience, 2005; 21: 637-646).

HIV Associated Dementia and Methamphetamine. A study showed that an increased risk of HIV-1 associated dementia (HAD) has been observed in patients abusing methamphetamine (METH). Since both HIV viral proteins (gp120, Tat) and METH induce oxidative stress, drug abusing patients are at a greater risk of oxidative stress-induced damage. CD-1 mice pre-treated with NACA/saline, received injections of gp120, Tat, gp120+ Tat or saline for 5 days, followed by three injections of MET-1H/saline on the fifth day, and sacrificed 24 h after the final injection. Various oxidative stress parameters were measured, and animals treated with gp120+Tat+Meth were found to be the most challenged group, as indicated by their GSH and MDA levels. Treatment with NACA significantly rescued the animals from oxidative stress. Further, NACA-treated animals had significantly higher expression of TJ proteins and BBB permeability as compared to the group treated with gp120+Tat+METH alone, indicating that NACA can protect the BBB from oxidative stress-induced damage in gp120, Tat and METH exposed animals, and thus could be a viable therapeutic option for patients with 1-AID (Banerjee A, Zhang X, Manda K R, Banks W A, Ercal N. HIV proteins (gp120 and Tat) and methamphetamine in oxidative stress-induced damage in the brain: Potential role of the thiol antioxidant N-acetylcysteine amide. Free Radic Biol Med. 2010 May 15; 48(10): 1388-1398. doi:10.1016/j.freeradbiomed.2010.02.023.)

Cocaine Abuse. A study demonstrated that NACA blocked cocaine-seeking behavior in olfactory bulbectomized rats (Jastrzębskal J, Frankowska M, Filip M, Atlas). N-acetylcysteine amide (AD4) reduces cocaine-induced reinstatement. Psychopharmacology 2016; 33:3437-3448 DOI 10.1007/s00213-016-4388-5).

Alcohol Abuse. Chronic alcohol intake leads to neuroinflammation and cell injury, proposed to result in alterations that perpetuate alcohol intake and cued relapse. Studies show that brain oxidative stress is consistently associated with alcohol□induced neuroinflammation, and literature implies that oxidative stress and neuroinflammation perpetuate each other. A study conducted on alcohol□preferring rats shows that chronic ethanol intake was inhibited by 50% to 55% by the oral administration of low doses of either the antioxidant NAC (40 mg/kg/d) or the anti-inflammatory aspirin (15 mg/kg/d), while the co□administration of both dugs led to a 70% to 75% ($p<0.001$) inhibition of chronic alcohol intake. Following chronic alcohol intake, a prolonged alcohol deprivation, and subsequent alcohol re□access, relapse drinking resulted in blood alcohol levels of 95 to 100 mg/dL in 60 minutes, which were reduced by 60% by either NAC or aspirin and by 85% by the co/administration of both drugs (blood alcohol: 10 to 15 mg/dL; $p<0.001$). Aspirin and NAC co□administration markedly inhibited chronic ethanol intake and blocked relapse binge drinking (Israel Y, Quintanilla M E, Ezquer F, Morales P, Santapau D, Berríos□Cárcamo P, Ezquer M, Olivares B, Herrera□Marschitz M. Aspirin and N□acetylcysteine co□administration markedly inhibit chronic ethanol intake and block relapse binge drinking: Role of neuroinflammation□oxidative stress self□perpetuation, Addiction Biology. 2019; e12853 https://doi.org/10.1111/adb.12853)

Blood Disorders. A study showed that in vitro treatment of blood cells from β-thalassemic patients with NACA elevated the reduced GSH content of red blood cells (RBC), platelets and polymorphonuclear (PMN) leukocytes, and reduced their reactive oxygen species (ROS). These effects resulted in a significant reduced sensitivity of thalassemic RBC to hemolysis and phagocytosis by macrophages. Intraperitoneal injection of NACA to β-thalassemic mice (150 ma/kg) significantly reduced the parameters of oxidative stress. NACA was shown to be superior to NAC in reducing oxidative stress markers in thalassemic cells both in vitro and in vivo. (Amer J, Atlas D, Fibach E. N-acetylcysteine amide (AD4) attenuates oxidative stress in beta-thalassemia blood cells. Biochimica et Biophysica Acta 1780 (2008) 249-255)

SUMMARY OF THE INVENTION

In accordance with an embodiment, the present invention provides a method for the use of diNACA to serve as a prodrug to NACA and NAC which are generated in vivo by metabolism of the prodrug diNACA. In accordance with an embodiment, the present invention provides a method for the use of NACA to serve as a prodrug to NAC which is generated in vivo by metabolism of the prodrug, NACA. NAC can also be generated from the prodrug, diNACA, by metabolism to NACA, then NAC. Therefore, it was found that both NACA and diNACA can serve as prodrugs to yield NAC in vivo, and therefore, are effective in prevention or treatment of any disease or disorder involving oxidative stress including but not limited to administering a therapeutically effective amount of diNACA, NACA, NAC, or combinations thereof to the mammal to prevent or treat one or more diseases or disorders of oxidative stress selected from AIDS, antivenom, beta-thalassemia, cataract, cataracts in a subject that does not have diabetes, chronic obstructive pulmonary disease, corneal endothelial cell loss, diabetes and diabetes-induced ulcers, macular degeneration, contrast-induced nephropathy, asthma, lung contusion, macular degeneration, methamphetamine-induced oxidative stress, multiple sclerosis, Parkinson's disease, platelet apoptosis, presbyopia, Tardive dyskinesia, Alzheimer disease, HIV, HIV-1-associated dementia, mitochondrial diseases, myocardial myopathy, neurodegenerative diseases, pulmonary fibrosis, retinitis pigmentosa, Usher syndrome, Stargardt syndrome, age-related macular degeneration, skin pigmentation, skin in need of rejuvenation, mucous accumulation or thickening in the respiratory system, low spermatogenesis and male infertility, beta-thalassemia, antimicrobial infection, HIV associated dementia, methamphetamine abuse, cocaine abuse, alcohol abuse, skin hyperpigmentation or Friedreich's ataxia.

In accordance with an embodiment, the present invention provides a method for the use of antioxidants, N-acetylcysteine amide (NACA) or (2R,2R')-3,3'-disulfanediyl bis(2-acetamidopropanamide) (diNACA) for the prevention or treatment of presbyopia. Further, in accordance with an embodiment, the present invention provides a method for the use of antioxidant, N-acetylcysteine amide (NACA) for the prevention of cataract, and (2R,2R')-3,3'-disulfanediyl bis(2-acetamidopropanamide) (diNACA) for prevention or treatment of cataract. In another aspect, the patient with cataracts does not have diabetes. In one non-limiting example, the prevention or reduction of oxidative stress associated with AIDS, antivenom, beta-thalassemia, cataract, chronic obstructive pulmonary disease, corneal endothelial cell loss, diabetes and diabetes-induced ulcers, macular degeneration, contrast-induced nephropathy, asthma, lung contusion, methamphetamine-induced oxidative stress, multiple sclerosis, Parkinson's disease, platelet apoptosis, presbyopia, Tardive dyskinesia, Alzheimer disease, HIV, HIV-1-associated dementia, mitochondrial diseases, myocardial myopathy, neurodegenerative diseases, pulmonary fibrosis, retinitis pigmentosa, Usher syndrome, Stargardt syndrome, age-related macular degeneration, skin pigmentation, skin in need of rejuvenation, antimicrobial infection, and/or Friedreich's ataxia in an animal or human that comprises administering to the animal or human a therapeutically effective amount of NACA or diNACA. In one aspect, the NACA or diNACA is provided in or with a pharmaceutically acceptable carrier. In another aspect, the NACA or diNACA is administered intraocularly, subretinally, intravitreally, orally, intravenously, intramuscularly, topically, sublingually, rectally or by injection, nasal spray or inhalation. In another aspect, NACA or diNACA is administered in daily doses of about 0.5 to 150 mg/Kg. In another aspect, NACA, or diNACA is administered two or three times daily. In another aspect, NACA or diNACA is administered with a second active agent selected from at least one of ascorbic acid, cysteine hydrochloride, sodium bisulfate, sodium metabisulfite, sodium sulfite, ascorbyl palmitate, butylated hydroxyanisole (BHA), butylated hydroxytoluene (BHT), lecithin, propyl gallate, α-tocopherol, citric acid, ethylenediamine tetraacetic acid (EDTA), sorbitol, tartaric acid, or phosphoric acid. In another aspect, the dose for administration is 100, 150, 150, 300, 333, 400, 500, 600, 700, 750, 800, 900, 1,000, 2,500, 5,000, 7,500, or 10,000 mg per dose. In another aspect, the dose for administration is 0.001-0.01, 0.01-0.1, 01-025, 0.1-0.4, 0.35-0.5, 0.5-1, 1-2, 1-3, 1-4, 1-5, 1-2.5, 2.5-3.5, 4-6, 5-8, 6-9, 7-10 grams per dose. In another aspect, NACA or diNACA is delivered orally via a mini-tablet, capsule, tablet, effervescent, dual release, mixed release, sachet, powder, or liquid. In another aspect, NACA or diNACA is administered prophylactically to prevent or reduce oxidative stress associated with AIDS, antivenom, beta-thalassemia, cataract, chronic obstructive pulmonary disease, corneal endothelial cell loss, diabetes and diabetes-induced ulcers, macular degeneration, contrast-induced nephropathy, asthma, lung contusion, methamphetamine-induced oxidative stress, multiple sclerosis, Parkinson's disease, platelet apoptosis, presbyopia, Tardive dyskinesia, Alzheimer disease, HIV, HIV-1-associated dementia, mitochondrial diseases, myocardial myopathy, neurodegenerative diseases, pulmonary fibrosis, retinitis pigmentosa, Usher syndrome, Stargardt syndrome, age-related macular degeneration, skin pigmentation, skin in need of rejuvenation, antimicrobial infection, and/or Friedreich's ataxia. In another aspect, the animal is a human. In another aspect, the patient with cataracts does not have diabetes.

In accordance with another embodiment, the present invention includes a method for the treatment of oxidative stress associated with AIDS, antivenom, beta-thalassemia, cataract, chronic obstructive pulmonary disease, corneal endothelial cell loss, diabetes and diabetes-induced ulcers, macular degeneration, contrast-induced nephropathy, asthma, lung contusion, methamphetamine-induced oxidative stress, multiple sclerosis, Parkinson's disease, platelet apoptosis, presbyopia, Tardive dyskinesia, Alzheimer disease, HIV, HIV-1-associated dementia, mitochondrial diseases, myocardial myopathy, neurodegenerative diseases, pulmonary fibrosis, retinitis pigmentosa, Usher syndrome, Stargardt syndrome, age-related macular degeneration, skin pigmentation, skin in need of rejuvenation, antimicrobial infection, and/or Friedreich's ataxia: identifying a human in need of treatment for oxidative stress associated with AIDS, antivenom, beta-thalassemia, cataract, chronic obstructive pulmonary disease, corneal endothelial cell loss, diabetes and diabetes-induced ulcers, macular degeneration, contrast-induced nephropathy, asthma, lung contusion, methamphetamine-induced oxidative stress, multiple sclerosis, Parkinson's disease, platelet apoptosis, presbyopia, Tardive dyskinesia, Alzheimer disease, HIV, HIV-1-associated dementia, mitochondrial diseases, myocardial myopathy, neurodegenerative diseases, pulmonary fibrosis, retinitis pigmentosa, Usher syndrome, Stargardt syndrome, age-related macular degeneration, skin pigmentation, skin in need of rejuvenation, antimicrobial infection, and/or Friedreich's ataxia; and administering to the human a therapeutically effective amount of N-acetylcysteine amide (NACA) or (2R,2R')-3,3'-disulfanediyl bis(2-acetamidopropanamide) (diNACA) sufficient to treat oxidative stress associated with AIDS, antivenom, beta-thalassemia, cataract, chronic obstructive pulmonary disease, corneal endothelial cell loss, diabetes and diabetes-induced ulcers, macular degeneration, contrast-induced nephropathy, asthma, lung contusion, methamphetamine-induced oxidative stress, multiple sclerosis, Parkinson's disease, platelet apoptosis, presbyopia, Tardive dyskinesia, Alzheimer disease, HIV, HIV-1-associated dementia, mitochondrial diseases, myocardial myopathy, neurodegenerative diseases, pulmonary fibrosis, retinitis pigmentosa, Usher syndrome, Stargardt syndrome, age-related macular degeneration, skin pigmentation, skin in need of rejuvenation, antimicrobial infection, and/or Friedreich's ataxia. In one non-limiting example, the prevention or reduction of corneal endothelial cell loss is in patients after cataract surgery. In one aspect, NACA or diNACA is provided in or with a pharmaceutically acceptable carrier. In another aspect, the NACA is administered intraocularly, subretinally, intravitreally, orally, intravenously, intramuscularly, topically, sublingually, or rectally. In another aspect, NACA or diNACA is administered in daily doses of about 0.005 to 150 mg/Kg. In another aspect, NACA or diNACA is administered two or three times daily. In another aspect, NACA or diNACA is administered with a second active agent selected from at least one of ascorbic acid, cysteine hydrochloride, sodium bisulfate, sodium metabisulfite, sodium sulfite, ascorbyl palmitate, butylated hydroxyanisole (BHA), butylated hydroxytoluene (BHT), lecithin, propyl gallate, α-tocopherol, citric acid, ethylenediamine tetraacetic acid (EDTA), sorbitol, tartaric acid, or phosphoric acid. In another aspect, the dose for administration is 0.01, 0.1, 1, 10, 100, 150, 150, 300, 333, 400, 500, 600, 700, 750, 800, 900, 1,000, 2,500, 5,000, 7,500, or 10,000 mg per dose. In another aspect, the does for administration is 0.01-0.1, 0.1-0.25, 0.1-0.4, 0.35-0.5, 0.5-1, 1-2, 1-3, 1-4, 1-5, 1-2.5, 2.5-3.5, 4-6, 5-8, 6-9, 7-10 grams per dose. In another aspect, the NACA or diNACA is delivered orally via a mini-tablet, capsule, tablet, effervescent, dual release, mixed release, sachet, powder, liquid, ocular insert, injection or implant. In another aspect, NACA or diNACA is administered prophylactically to prevent or reduce oxidative stress associated with corneal endothelial cell loss. In another aspect, the patient with cataracts does not have diabetes.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
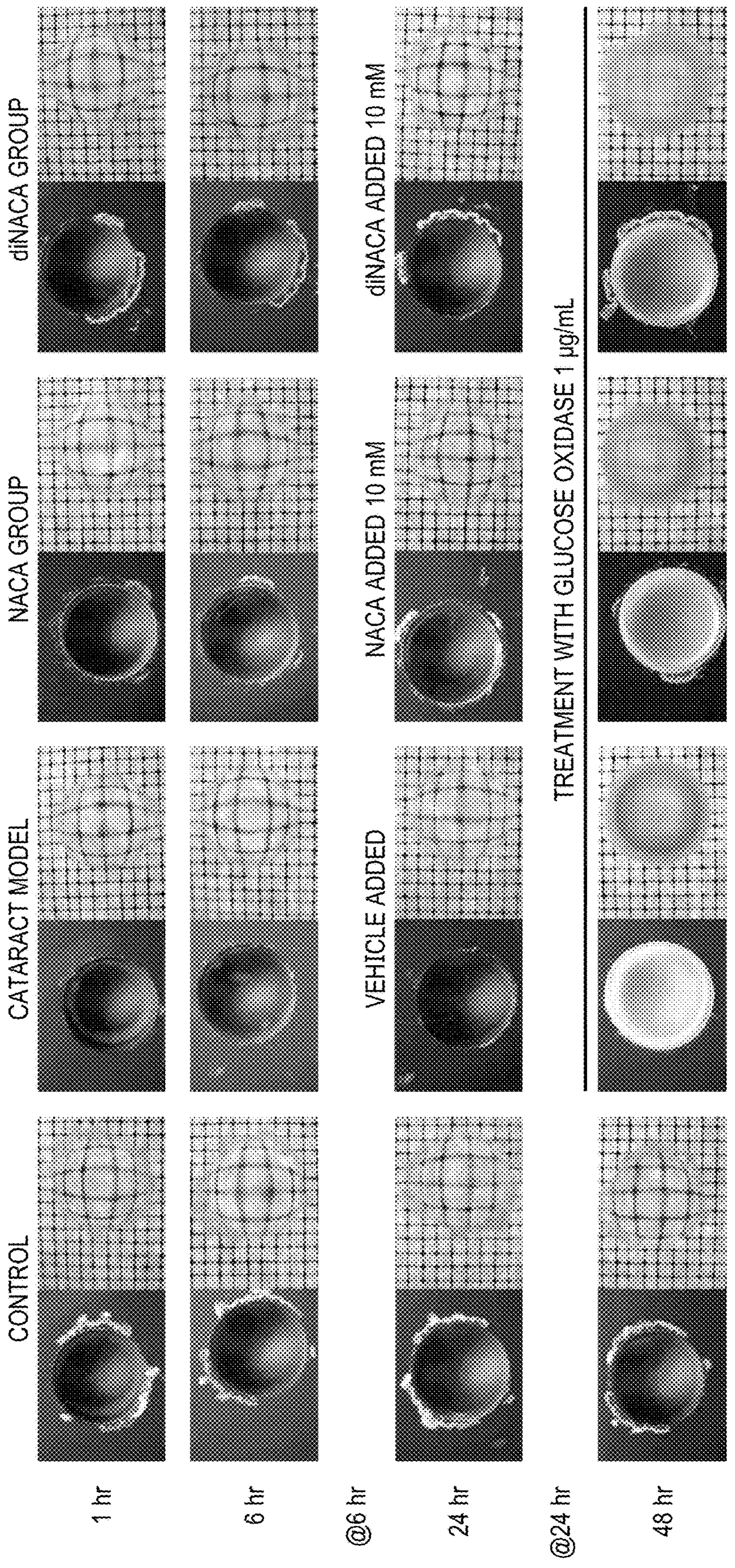
FIG. 1 shows that NACA and diNACA inhibit oxidative formation of cataract (opacity) in isolated rat lens based on comparison to control ("cataract model").

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The present invention relates in general to the use of (2R,2R')-3,3'-disulfanediyl bis(2-acetamidopropanamide) (diNACA) as a prodrug to NACA and NAC for the prevention and/or treatment of various diseases and/or disorders involving oxidative stress. The present invention also relates in general to the use of NACA as a prodrug to NAC for the prevention and/or treatment of various diseases and/or disorders involving oxidative stress. Diseases or disorders involving oxidative stress include but are not limited to AIDS, alcohol or substance abuse, antivenom, beta-thalassemia, cancer, cataract, chronic obstructive pulmonary disease, corneal endothelial cell loss, covid-19, cystinosis, diabetes and diabetes-induced ulcers, macular degeneration, contrast-induced nephropathy, asthma, lung contusion, methamphetamine-induced oxidative stress, multiple sclerosis, Parkinson's disease, platelet apoptosis, presbyopia, Tardive dyskinesia, Alzheimer disease, HIV, HIV-1-associated dementia, mitochondrial diseases, myocardial myopathy, neurodegenerative diseases, pulmonary fibrosis, retinitis pigmentosa, Usher syndrome, Stargardt syndrome, age-related macular degeneration, skin pigmentation, skin in need of rejuvenation, low spermatogenesis and infertility in males, antimicrobial infection, and/or Friedreich's ataxia.

DiNACA can be used for the treatment of ophthalmic conditions caused by oxidative stress including prevention and treatment of cataract, corneal endothelial cell loss and presbyopia. In addition, NACA or NAC can be used to prevent or treat presbyopia. Further, NACA can be used to treat corneal endothelial cell loss. In addition, diNACA can be used to treat substance abuse disorders.

N-acetylcysteine, also known as 2-acetamido-3-sulfanylpropanoic acid or NAC, has the chemical structure:

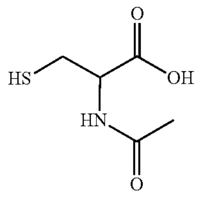

N-acetylcysteine (NAC) has shown a potential role in protecting lens against oxidative-induced cataracts, preventing post-vitrectomy cataracts, or inhibiting the progression of diabetic cataract at the earlier stage. (Wang P, Liu X C, Yan H, Li M Y. Hyperoxia-induced lens damage in rabbit: protective effects of N-acetylcysteine. Mol Vis. 2009; 15:2945-52; Liu X C, Wang P, Yan H. A rabbit model to study biochemical damage to the lens after vitrectomy: effects of N-acetylcysteine. Exp Eye Res. 2009; 88(6):1165-70. doi: 10.1016/j.exer.2009.01.001; Zhang S, Chai F Y, Yan H, Guo Y, Harding J, Effects of N-acetylcysteine and glutathione ethyl ester drops on streptozotocin-induced diabetic cataract in rats. Mol Vis. 2008; 14:862-70.)

N-acetylcysteine amide (NACA), also known as (R)-2-(acetylamino)-3-mercapto-propanamide, N-acetyl-L-cysteinamide, or acetylcysteinamide, has the chemical structure:

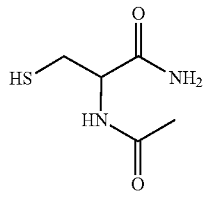

N-acetylcysteine amide (NACA), the amide form of N-acetyl-L-cysteine (NAC), is a small molecule thiol antioxidant and a copper chelator. NACA provides protective effects against cell damage. NACA has been shown to inhibit t-butylhydroxyperoxide (BuOOH)-induced intracellular oxidation in RBCs and to retard BuOOH-induced thiol depletion and hemoglobin oxidation in the RBCs superior to NAC. (L. Grinberg et al., Free Radical Biol Med. 2005; 38(1):136-45.). NACA was shown to react with oxidized glutathione (GSSG) to generate reduced GSH. NACA readily permeates cell membranes better than NAC. Since NACA is neutral, as contrasted with NAC which is acidic, NACA has greater lipophilicity and cell permeability than NAC (Atlas D et al., U.S. Pat. No. 5,874,468). NACA has been shown to inhibit sodium selenite-induced (Maddirala et al. BMC Ophthalmology (2017) 17:54) and 1-buthionine-(S,R)-induced cataracts (Carey J W, Pinarci E Y, Penugonda S, Karacal H, Ercal N. In vivo inhibition of 1-buthionine-(S,R)-sulfoximine-induced cataracts by a novel antioxidant, N-acetylcysteine amide. Free Radical Biol Med. 2011; 15; 50(6):722-9. doi: 10.1016/j.Free Rad Biol Med.2010.12.017.).

(2R,2R')-3,3'-disulfanediyl bis(2-acetamidopropanamide) (diNACA, NPI-002), has the chemical structure:

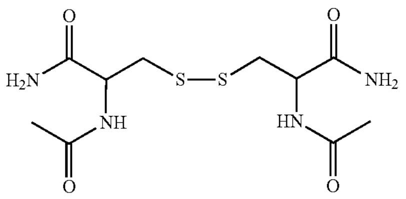 [SMILES: CC(=O)NC(CSSCC(NC(C)=O)C(N)=O)C(N)=O]

(2R,2R')-3,3'-disulfanediyl bis(2-acetamidopropanamide) (diNACA), the dimer form of N-acetylcysteine amide is a synthetic precursor to NACA (AU2018365900132). DiNACA is a prodrug to NACA and NAC which are metabolites of diNACA. Therefore, any disease or disorder associated with oxidative stress that can be treated with NAC or NACA is likely amenable to treatment with diNACA including, but not limited to AIDS, antivenom, beta-thalassemia, cataract, chronic obstructive pulmonary disease, corneal endothelial cell loss, diabetes and diabetes-induced ulcers, macular degeneration, contrast-induced nephropathy, asthma, lung contusion, methamphetamine-induced oxidative stress, multiple sclerosis, Parkinson's disease, platelet apoptosis, presbyopia, Tardive dyskinesia, Alzheimer disease, HIV, HIV-1-associated dementia, mitochondrial diseases, myocardial myopathy, neurodegenerative diseases, pulmonary fibrosis, retinitis pigmentosa, Usher syndrome, Stargardt syndrome, age-related macular degeneration, skin pigmentation, skin in need of rejuvenation, antimicrobial infection, and/or Friedreich's ataxia. In another example, the patient with cataracts does not have diabetes.

The present invention can be used in pharmaceutical compositions for use in the treatment of human diseases and disorders such as those outlined above. Typically such compositions further comprise a pharmaceutically acceptable (i.e. inert) carrier as known and called for by acceptable pharmaceutical practice, see e.g. Remington's Pharmaceutical Sciences, 16th ed, (1980), Mack Publishing Co. Examples of such carriers include sterilized carrier such as saline, Ringer's solution, dextrose solution, phosphate buffered saline, aqueous or non-aqueous solution, buffered solutions with suitable buffers such as sodium acetate trihydrate to a pharmaceutically acceptable pH, such as a pH within a range of 5 to 8. Pharmaceutical compositions for injection (e.g., by oral, intravenous, intraperitoneal, intradermal, subcutaneous, intramuscular, intraportal or by local delivery to the eye by topical or periocular application to the eye or intravitreal injection into the eye) or continuous infusion are suitably free of visible particulate matter and may comprise diNACA NAC, NACA, individually or in combinations as taught herein. Further, pharmaceutical compositions for use in the treatment of human diseases and disorders such as those outlined above may also comprise polymeric vehicles, bioerodible or non-bioerodable, such as inserts or implants, from which the prodrug elutes when placed near or in tissue.

Gluthathione (GSH) is a tripeptide, c-L-glutamyl-L-cysteinyl-glycine, found in all mammalian tissues. It has several important functions including detoxification of electrophiles, scavenging ROS, maintaining the thiol status of proteins, and regeneration of the reduced forms of vitamins C and E. GSH is the dominant non-protein thiol in mammalian cells; as such it is essential in maintaining the intracellular redox balance and the essential thiol status of proteins. Also, it is necessary for the function of some antioxidant enzymes such as the glutathione peroxidases.

Protocol for inhibition of oxidation of isolated rat lenses. Three-week old Wistar rat eyes were enucleated and lenses micro-dissected in Dulbecco's modified eagle's medium (low glucose) (DMEM-F12). Lenses were handled using only custom-made glass loops to avoid changes in transparency and placed in 1 mL DMEM with 1% penicillin/streptomycin/neomycin. Lenses were placed in a culture incubator set at 37° C./5% $CO_2$ for one hour. Then lenses were imaged under darkfield and brightfield (grid) to ensure they are still transparent before adding vehicle (H2O), 10 mM NACA (solution), or 10 mM diNACA (suspension). Lenses were then imaged at a 6-hour time period to ensure transparency was maintained, then incubated for another 18 hours, then imaged again (total 24 hour incubation). Media was collected and fresh media was added to the wells. 0.5 mM $H_2O_2$ (warmed at 37 deg C.) was added and left for a further 24-hour incubation. Lenses were imaged, media collected, lenses weighed and flash frozen in tared vials and submitted for further analysis FIG. 1 shows that NACA and diNACA inhibit oxidative formation of cataract (opacity) in isolated rat lens based on comparison to control ("cataract model").

Figure 2:
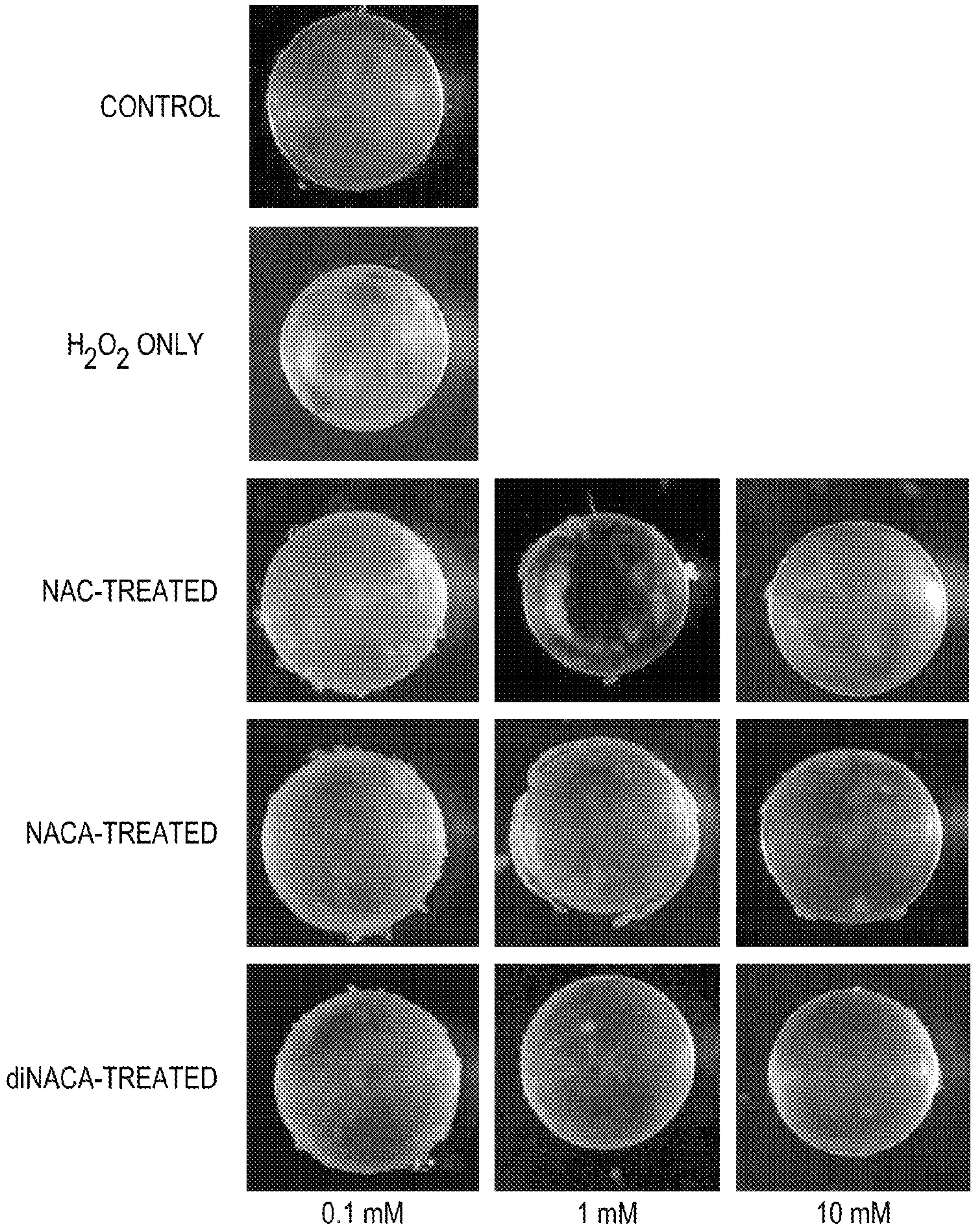
FIG. 2 shows that NAC, NACA and diNACA can dose-dependently prevent $H_2O$-induced cataract in isolated porcine lenses. NACA and diNACA exhibit greater efficacy than NAC.

Protocol for inhibition of oxidation of isolated porcine lenses. Fresh eyes from pigs were obtained from Sierra For Medical Science. Lenses were first incubated in medium 199 (Sigma-Aldrich, St. Louis, MO, USA) and 1% pig serum in a 12-well plate for two hours. At the end of the incubation, lenses were imaged under darkfield microscopy and only clear, transparent lenses were used for further experimentation. Lenses were then pre-incubated with NAC, NACA or diNACA for 24 hours. After pretreatment, lenses were transferred to media containing 600 μM $H_2O_2$ which was supplemented with glucose oxidase (GO) for maintaining a constant $H_2O_2$ level during further incubation for 6 hours [Wang G M, Raghavachari N, Lou M F. Relationship of protein-glutathione mixed disulfide and thioltransferase in H2O2-induced cataract in cultured pig lens. Exp Eye Res. 1997 May; 64(5):693-700. doi: 10.1006/exer.1996.0251. PMID: 9245898.]. At the end of the 6-hour incubation, lenses were imaged under darkfield microscopy FIG. 2 shows that NAC, NACA and diNACA dose-dependently inhibit H2O2-induced cataract in isolated porcine lenses. NACA and diNACA exhibit greater efficacy than NAC.

Protocol for corneal endothelial cell protection. Cell viability was measured by a colorimetric cell viability kit (Cayman, Ann Arbor, Michigan) with the tetrazolium salt WST-8 (2-(2-methoxy-4-nitrophenyl)-3-(4-nitrophenyl)-5-(2,4-disulfophenyl)-2H-tetrazolium, monosodium salt), which was bioreduced to a water-soluble orange formazan dye by dehydrogenases present in the viable cells. The amount of formazan produced was directly proportional to the number of living cells. Cells were seeded at a density of 6000 cells/well (100 μl total volume/well) in a 96-well assay. Cells (n=8) were incubated with or without different concentrations of NAC, NACA, and diNACA (2, 20, and 40 mM) for 48 h and then treated with 500 μM of tert-butyl hydroperoxide (tBHP) for additional 4 hours. After treatment, 10 μl of WST-8 solution was added to each well of the culture plate and incubated for 4 hours in the incubator. The absorption was evaluated at 450 nm using a microplate reader (BioTek, Winooski, VT).

Figure 3:
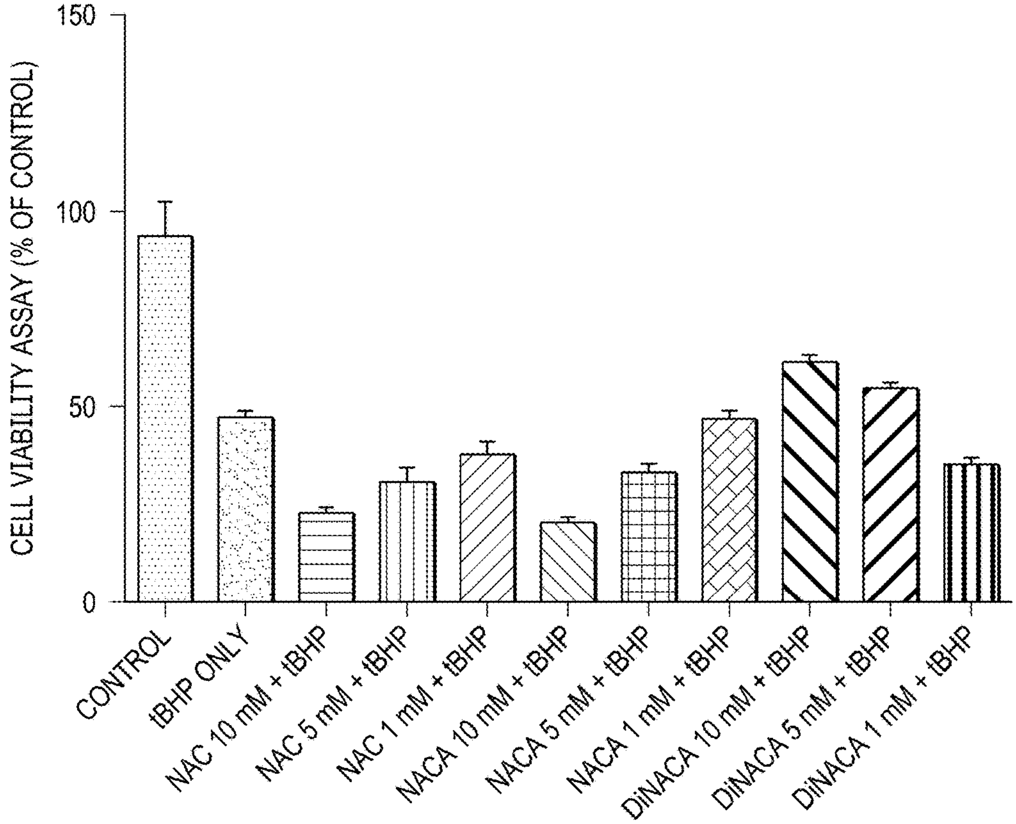
FIG. 3 is a graph that shows the effect of NAC, NACA, and diNACA pretreatment for 24 hours followed by tBHP treatment and incubation for 4 hours.
Figure 4:
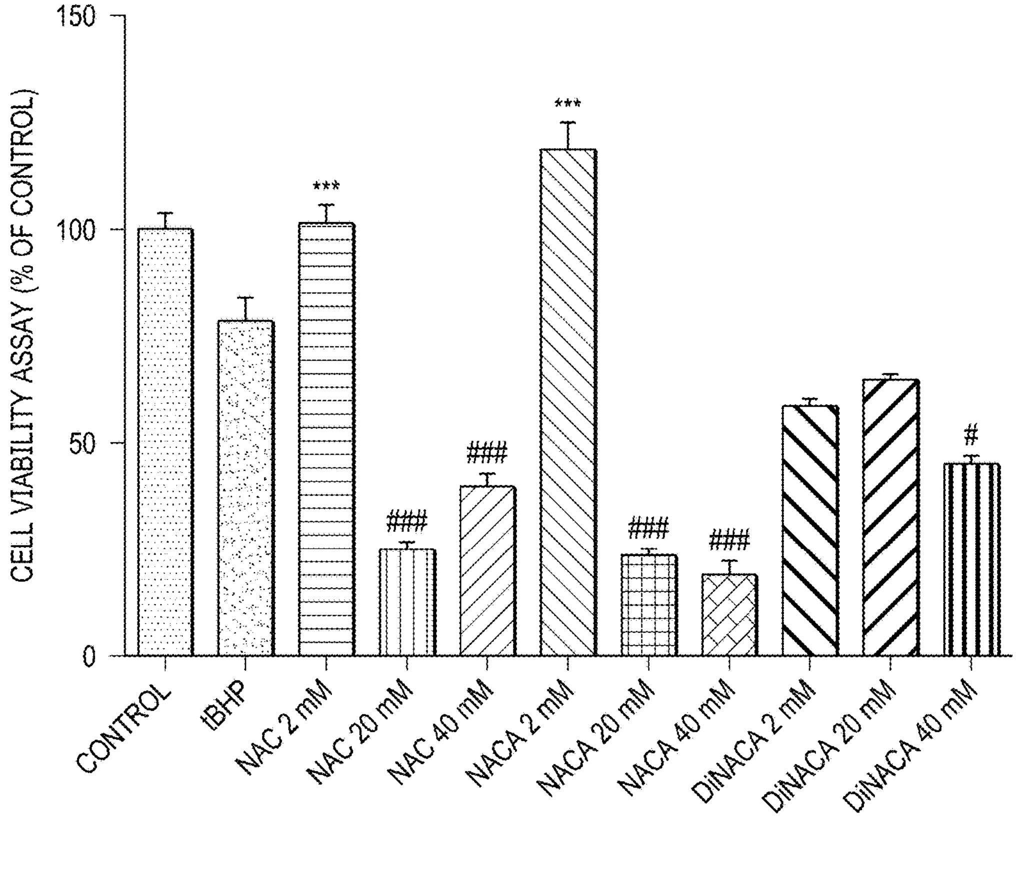
FIG. 4 is a graph that shows the effect of NAC, NACA, and diNACA pretreatment for 48 hours followed by tBHP treatment and incubation for 4 hours (*** P<0.0001 (protection) compared with tBHP only; #P<0.05 compared with tBHP only; #4 #P<0.001 compared with tBHP only).

FIG. 3 is a graph that shows the effect of NAC, NACA, and diNACA pretreatment for 24 hours followed by tBHP treatment and incubation for 4 hours. FIG. 4 is a graph that shows the effect of NAC, NACA and diNACA pretreatment for 48 hours followed by tBHP treatment and incubation for 4 hours (* $P<0.0001$ (protection) compared with tBHP only; #$P<0.05$ compared with tBHP only; ###$P<0.001$ compared with tBHP only). Comparison of cell viability assay results in FIG. 4 to FIG. 3** shows that longer pretreatment with antioxidants yields greater protection of cells against oxidation.

Intracellular GSH levels are determined by the balance between production and loss. Production results from de novo synthesis and regeneration of GSH from GSSG by GSSG reductase. Generally, there is sufficient capacity in the GSSG reductase system to maintain all intracellular GSH in the reduced state, so little can be gained by ramping up that pathway. The major source of loss of intracellular GSH is transport out of cells. Intracellular GSH levels range from 1-8 mM while extracellular levels are only a few μM this large concentration gradient essentially precludes transport of GSH into cells and once it is transported out of cells, it is rapidly degraded by γ-glutamyltranspeptidase. Inhibition of GSH transporters could theoretically increase intracellular GSH levels but is potentially problematic because the transporters are not specific for GSH and their suppression could lead imbalance of other amino acids and peptides. Thus, intracellular GSH levels are modulated primarily by changes in synthesis.

GSH is synthesized in the cytosol of virtually all cells by two ATP-requiring enzymatic steps: L-glutamate+L-cysteine+ATP[→]γ-glutamyl-L-cysteine+ADP+25 Pi and γ-glutamyl-L-cysteine+L-glycine+ATP[→]GSH+ADP+Pi. The first reaction is rate-limiting and is catalyzed by glutamate cysteine ligase (GCL, EC 6.312.2). GCL is composed of a 73 Kd heavy catalytic subunit (GCLC) and a 30 Kd modifier subunit (GCLM), which are encoded by different genes. CCCL is regulated by nonallosteric competitive inhibition of GSH (Ki=2.3 mM) and by the availability of L cysteine. The apparent $K_m$ of GLC for glutamate is 1.8 mM and intracellular glutamate concentration is roughly 10-fold higher so that glutamate is not limiting, but the Km for cysteine is 0.1-0.3 nM, which approximates its intracellular concentration. The second reaction is catalyzed by GSH synthase (GS, EC 6.3.2.3), which is 118 Kd and composed of two identical subunits. While GS is not felt to be important in regulation of GSH synthesis under normal conditions, it may play a role tinder stressful conditions because in response to surgical trauma, GSH levels and GS activity were reduced while GCL activity was unchanged. Furthermore, compared to increased expression of GCLC alone, increased expression of both GCLC and GS resulted in higher levels of CSH. In order to maximize the effects of increasing synthetic enzymes, it is necessary to provide increased levels of cysteine. In cultured neurons, 90% of cysteine uptake occurs through by the sodium-dependent excitatory amino acid transporter (EAAT) system. There are five EAATs and cysteine uptake by neurons occurs predominantly by EAAT3 more commonly known as excitatory amino acid carrier-1 (EAAC1). Under normal circumstances most EAAC1 is in the ER and only translocates to the plasma membrane when activated. This translocation is negatively regulated by glutamate transporter associated protein 3-18 (GTRAP3-18) and suppression of GTRAP3-18) increased GSH levels in neurons. Thus, internalization of cysteine provides a road block for GSH synthesis, but fortunately it can be bypassed by N-acetylcysteine (NAC) which readily enters cells even in the absence of activated EAAC1. Systemically administered NAC gains access to the CNS, increases GSH levels, and provides benefit in neurodegenerative disorders in which oxidative stress is an important part of the pathogenesis.

All cellular compartments must be protected against oxidative damage, including the cytoplasm, mitochondria and the nucleus. The present inventors have previously performed gene transfer of enzymes that detoxify reactive oxygen species, but that approach requires expression of two enzymes in the cytoplasm and two enzymes in mitochondria. In contrast, the present invention provides for protection of all cellular compartments with expression of only two enzymes in the cytosol because GSH diffuses throughout cells.

NAC is used for the treatment of acetaminophen overdose at a dose of 140 mg/kg as the loading dose, followed by 70 mg/kg every 4 hours for 17 doses, starting 4 hours after the loading dose. In clinical studies, NAC has been administered orally from 400 to 1000 mg once daily and from 200 to 600 mg three times daily. However, following an oral dose of 600 mg in humans, NAC is rapidly absorbed and then rapidly cleared. The plasma half-life of NAC has been reported to be 2.5 hours and no NAC is detectable 10-12 hours after administration. During absorption, NAC is rapidly metabolized to cysteine, which is a direct precursor of glutathione. In accordance with an embodiment, the present invention provides a method for the prevention, amelioration, or treatment of a disease or condition associated with oxidative stress in a subject comprising administration of a therapeutically effective amount of NACA or diNACA to increase the amount of NAC, hence, glutathione expressed in the tissues of the subject.

Figure 5:
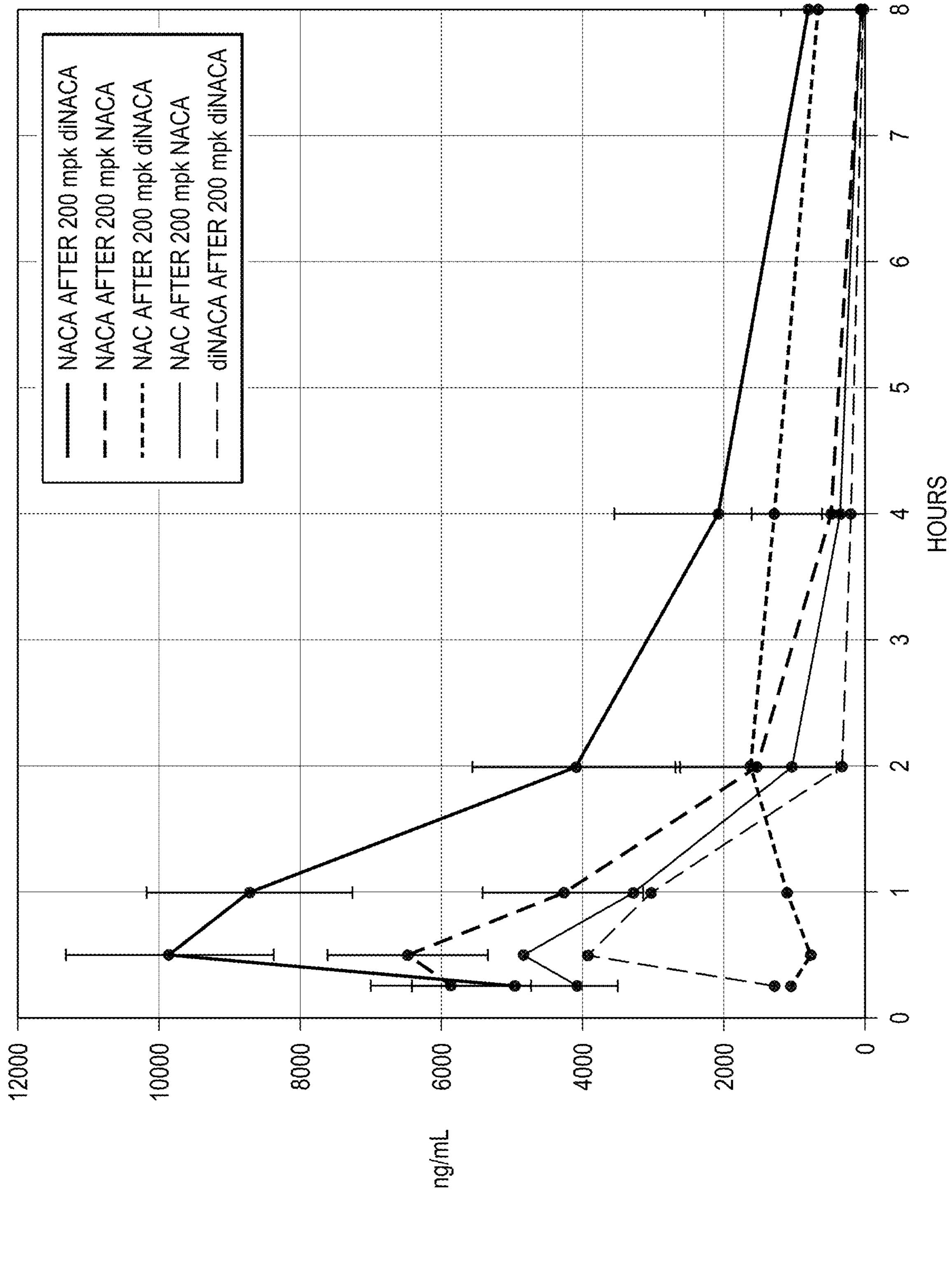
FIG. 5 shows that diNACA is bioavailable after oral administration in rat and that oral administration of diNACA yields significant levels of diNACA, NAC A and NAC in rat plasma.

DiNACA as a Prodrug to NACA and NAC. Example 1: Oral Dose Study in Rat. An IACUC (Institutional Animal Care and Use Committee)-approved study evaluated diNACA dosed via oral gavage in male Sprague-Dawley rats. diNACA was weighed into individual tubes. The tubes were capped and stored at room temperature overnight. Rats were weighed. An appropriate amount of phosphate buffered saline pH 7.0 was added to each tube to achieve the desired diNACA concentration as a suspension. Blood specimens were collected from the tail vein at specified time points and processed to produce plasma. Plasma specimens were analyzed using a validated liquid chromatographic mass spectrometric procedure (King B; Vance J; Wall G M; Shoup R. Quantitation of free and total N-acetylcysteine amide and its metabolite N-acetylcysteine in human plasma using derivatization and electrospray LC-MS/MS. J Chrom B 2019; 1109:25-36.). FIG. 5 shows the levels of diNACA, NACA and NAC achieved in rat plasma following oral gavage of diNACA 200 milligrams per kilogram in rat. This study demonstrates that diNACA serves as a prodrug to NACA and NAC.

Example 2: Topical Ocular Study in Rabbit. An IACUC-approved study evaluated diNACA or NACA topical ocular dosing in rabbit. Ophthalmic formulations were developed containing either 1% diNACA or 1% NACA that were used for repeated topical ocular instillation to Dutch Belted rabbits. Animals were dosed four times a day at approximately 8:00 AM, 11 AM, 2 PM, and 4:00 PM on days 1-6, and once on Day 7 at approximately 8:00 AM, via bilateral topical administration. Ocular tolerability was assessed at baseline and prior to the first daily dose by means of scoring chemosis, discharge, and hyperemia (Draize scoring). Ocular tissue was harvested at necropsy (day 7). A qualified analytical LC-MS method was developed and used to quantitate NACA levels in aqueous humor (All). No serious adverse findings were observed following topical ocular dosing. Table I shows levels of NACA achieved in aqueous humor following dosing of either 1% diNACA or 1%. The presence of diNACA in the AH demonstrated that diNACA penetrates the eye following topical ocular dosing. The presence of NACA in the AH demonstrated that diNACA served as a prodrug to deliver NACA to the AH.

TABLE I

Levels of NACA achieved in aqueous humor following topical dosing in rabbits of either 1% diNACA or 1% NACA (BLQ: below limit of quantitation).

| Subject Number | Arm | Treatment | Eye | NACA in Aqueous Humor (ng/mL) |
|---|---|---|---|---|
| 1337 | 1 | 1% NACA | Left | 51.4 |
| | 1 | 1% NACA | Right | 23.7 |
| 1338 | 1 | 1% NACA | Left | 64.9 |
| | 1 | 1% NACA | Right | BLQ < (20.0) |
| 1339 | 1 | 1% NACA | Left | 33.5 |
| | 1 | 1% NACA | Right | BLQ < (20.0) |
| 1340 | 2 | 1% diNACA | Left | 56.3 |
| | 2 | 1% diNACA | Right | BLQ < (20.0) |
| 1341 | 2 | 1% diNACA | Left | 33.7 |
| | 2 | 1% diNACA | Right | 47.7 |
| 1342 | 2 | 1% diNACA | Left | 85.4 |
| | 2 | 1% diNACA | Right | 35.3 |

Figure 6:
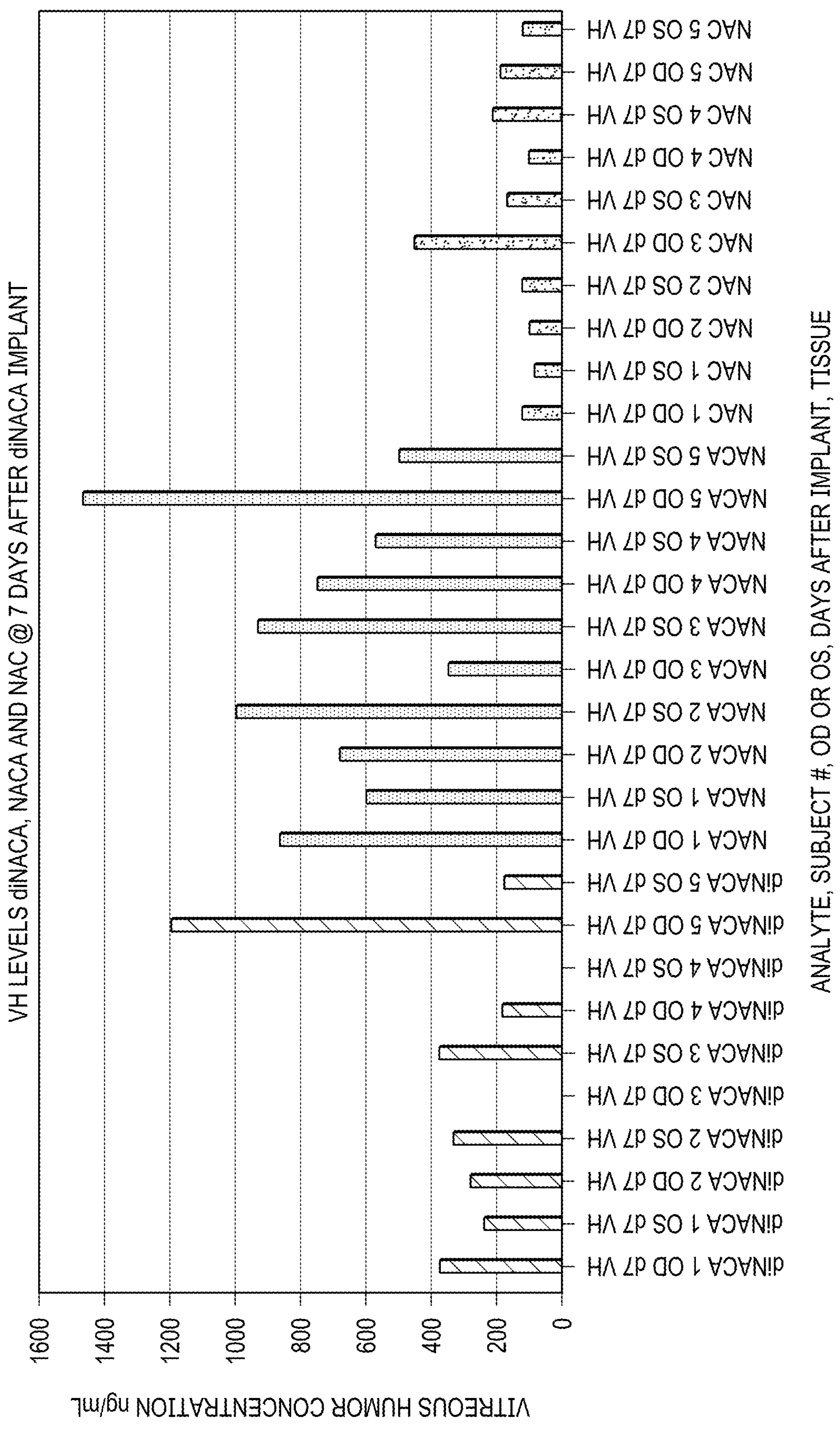
FIG. 6 shows levels of diNACA, NACA and NAC at 7 days post-implantation of diNACA intravitreal implant.
Figure 7:
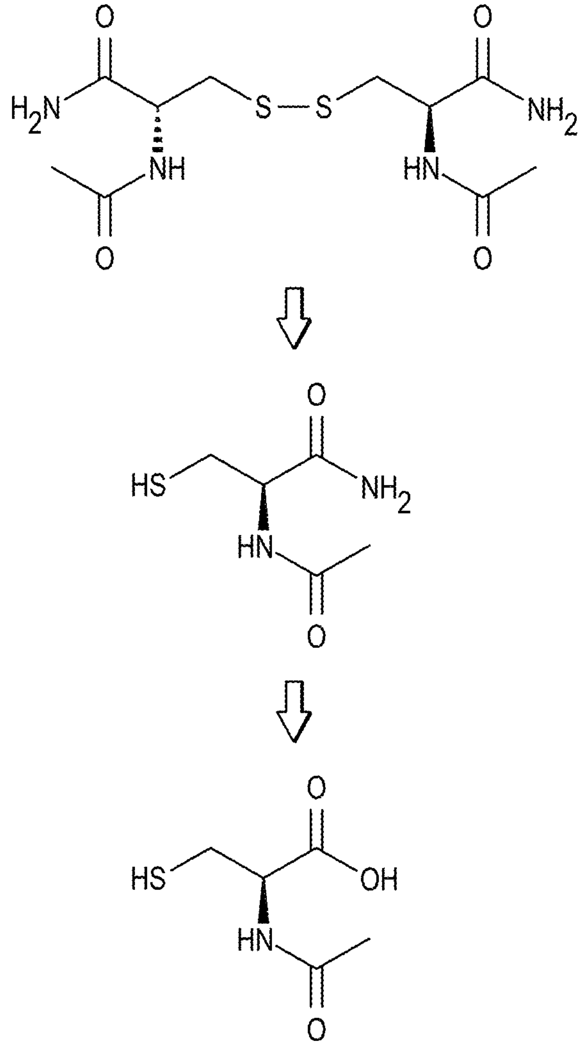
FIG. 7 shows the generation of NACA and NAC as metabolites of diNACA, the prodrug, following IVT administration.

Example 3: Intravitreal Dose Study in Rabbit. An IACUC-approved study evaluated intravitreally (IVT) dosed diNACA in rabbit. A standard sterile intravitreal implant containing diNACA was prepared. Female New Zealand White rabbits were administered IVT with a di-NACA implant at a dose of 0.8 mg/eye. One group of animals received IVT placebo implants without any test article. Clinical ophthalmic examinations were performed at baseline and on Days 8 and 23 post-dose. General health observations were performed daily. Body weights were recorded at baseline and prior to termination. Animals were euthanized on Day 8, 15, or 23, and tissue was collected and submitted for bioanalysis. Delivery of IVT di-NACA was associated with minimal ocular findings on the day of dosing. Observations of conjunctival bulging, discharge, and minimal hemorrhaging were determined to be related to the injection procedure and resolved in most eyes on the day after dosing. Mild to moderate conjunctival congestion, swelling and discharge observed on Day 8 by clinical ophthalmic examinations were resolved by Day 23, suggesting that these findings were associated with the use of 22-gauge needle for IVT injection procedure. No serious adverse effects of test article administration on general, non-ocular health or on body weights were observed. In summary, delivery of IVT di-NACA was generally well tolerated. FIG. 6 shows levels of diNACA, NACA and NAC at 7 days post-implant of diNACA IVT implant. FIG. 7 shows the generation of NACA and NAC as metabolites of diNACA, the prodrug, following IVT administration. The presence of diNACA in the vitreous humor (VH) demonstrated that diNACA eluted into the VH from the IVT implant. The presence of NACA and significant concentrations of NAC in the VH demonstrated that diNACA served as a prodrug to NACA and NAC.

As used herein, “active oxygen species” or “reactive oxygen species” are understood as transfer of one or two electrons produces superoxide, an anion with the form $O_2$", or peroxide anions, having the formula $O_2$_" or compounds containing an O—O single bond, for example hydrogen peroxides and lipid peroxides. Such superoxides and peroxides are highly reactive and can cause damage to cellular components including proteins, nucleic acids, and lipids.

As used herein, the terin "agent" refers to a therapeutically active compounds or a potentially therapeutic active compound, e.g., an antioxidant. An agent can be a previously known or unknown compound. As used herein, an agent is typically a non-cell based compound, however, an agent can include a biological therapeutic agent, e.g., peptide or nucleic acid therapeutic, e.g., siRNA, shRNA, cytokine, antibody, etc.

Oxidation is a chemical reaction that transfers electrons from a substance to an oxidizing agent. Such reactions can be promoted by or produce superoxide anions or peroxides. Oxidation reactions can produce free radicals, which start chain reaction that damage cells. Antioxidants terminate these chain reactions by removing free radical intermediates, and inhibit other oxidation reactions by being oxidized themselves. As a result, antioxidants are often reducing agents such as thiols, ascorbic acid or polyphenols. Antioxidants include, but are not limited to, α-tocopherol, ascorbic acid, Mn(III)tetrakis(4-benzoic acid) porphyrin, α-lipoic acid, and n-acetylcysteine.

As used herein, the terms "effective amount" or "effective doses" refer to that amount of an agent to product the intended pharmacological, therapeutic or preventive results. The pharmacologically effective amount results in the amelioration of one or more signs or symptoms of a disease or condition or the advancement of a disease or conditions, or causes the regression of the disease or condition. For example, a therapeutically effective amount preferably refers to the amount of a therapeutic agent that decreases vision loss, the loss of overall visual acuity, the loss of visual field, by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more as compared to an untreated control subject over a defined period of time, e.g., 2 weeks, one month, 2 months, 3 months, 6 months, one year, 2 years, 5 years, or longer. More than one dose may be required to provide an effective dose.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such as treatment may be ineffective in a subgroup that can be identified by the expression profile or profiles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as an improvement of symptoms, a cure, a reduction in disease signs or symptoms, extension of life, improvement in quality of life, or other effect generally recognized as positive by medical doctors familiar with treating the particular type of disease or condition.

As used herein, the terms "peroxidases" or "a peroxide metabolizing enzyme" refer to a large family of enzymes that typically catalyze a reaction of the form:

$ROOR_1$+electron donor (2 e−)+2H+→ROH+$R_1$OH For many of these enzymes the optimal substrate is hydrogen peroxide, wherein each R is H, but others are more active with organic hydroperoxides such as lipid peroxides. Peroxidases can contain a heme cofactor in their active sites, or redox-active cysteine or selenocysteine residues.

As used herein, the term phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. For example, pharmaceutically acceptable carriers for administration of cells typically is a carrier acceptable for delivery by injection, and do not include agents such as detergents or other compounds that could damage the cells to be delivered. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; tale; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen free water; isotonic saline; Ringer's solution; ethyl alcohol; phosphate buffer solutions; and other non-toxic compatible substances employed in pharmaceutical formulations, particularly phosphate buffered saline solutions which are preferred for intraocular delivery.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, t-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, intramuscular, intraperotineal, intraocular, intravitreal, subretinal, and/or other routes of parenteral administration. The specific route of administration will depend, inter alia, on the specific cell to be targeted. The formulations may conveniently be presented in unit dosage form and may be prepared by any methods well known in the art of pharmacy.

The amount of active ingredient that can be combined with a carrier material to produce a single dosage form will generally be that amount of the compound that produces a therapeutic effect.

As used herein, "plurality" is understood to mean more than one. For example, a plurality refers to at least two, three, four, five, or more.

As used herein, the term a "polypeptide" or "peptide" is understood as two or more independently selected natural or non-natural amino acids joined by a covalent bond (e.g., a peptide bond). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full-length proteins (e.g., fully processed proteins) as well as shorter amino acids sequences (e.g., fragments of naturally occurring proteins or synthetic polypeptide fragments).

As used herein, the term "small molecule" refers to a compound, typically an organic compound, having a molecular weight of no more than about 1500 Da, 1000 Da, 750 Da, or 500 Da. In an embodiment, a small molecule does not include a polypeptide or nucleic acid including only natural amino acids and/or nucleotides.

As used herein, the term "subject" refers to living organisms, in particular, humans. In certain embodiments, the living organism is an animal, in certain preferred embodiments, the subject is a mammal, in certain embodiments, the subject is a domesticated mammal or a primate including a non-human primate. Examples of subject include humans, monkeys, dogs, cats, mice, rates, cows, horses, goats, and sheep. A human subject may also be referred to as a subject or patient.

As used herein, "superoxide dismutase" is understood as an enzyme that dismutation of superoxide into oxygen and hydrogen peroxide. Examples include, but are not limited to SOD1, SOD2, and SOD3. Sod1 and SOD3 are two isoforms of Cu—Zn-containing superoxide dismutase enzymes exists in mammals. Cu—Zn-SOD or SOD1, is found in the intracellular space, and extracellular SOD (ECSOD or SOD3) predominantly is found in the extracellular matrix of most tissues.

As used herein, the term "therapeutically effective amount," refers to an amount of an agent which is effective, upon single or multiple does administration to the cell or subject, in prolonging the survivability of the patient with such a disorder, reducing one or more signs or symptoms of the disorder, preventing or delaying and the like beyond that expected in the absence of such treatment.

An agent or other therapeutic intervention can be administered to a subject, either alone or in combination with one or more additional therapeutic agents or interventions, as a pharmaceutical composition in mixture with conventional excipient, e.g., pharmaceutically acceptable carrier, or therapeutic treatments.

The pharmaceutical agents may be conveniently administered in unit dosage form and may be prepared by any of the methods well known in the pharmaceutical arts, e.g., as described in Remington's Pharmaceutical Sciences (Mack Pub. Co., Easton, PA, 1985), Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain agents.

The present invention is directed to the use of NACA and/or diNACA to treat, prevent or reduce a number of diseases or conditions of oxidative stress including corneal endothelial cell loss. In one embodiment, the present invention includes a method for use of NACA and/or diNACA for the prevention of corneal endothelial cell loss in patients, e.g., after cataract surgery in a human that comprises administering to the human therapeutically effective amount of NACA and/or diNACA. In some embodiments, NACA and/or diNACA is provided in or with a pharmaceutically acceptable carrier. In other embodiments, the NACA and/or diNACA is administered intraocularly, subretinally, intravitreally, orally, intravenously, intramuscularly, topically, sublingually, rectally, ocularly (eyedrops, insert, injection or implant).

It will be appreciated that the actual preferred amounts of active compounds used in a given therapy will vary according to e.g., the specific compound being utilized, the particular composition formulated, the mode of administration and characteristics of the subject, e.g., the species, sex, weight, general health and age of the subject. Optimal administration rates for a given protocol of administration can be readily ascertained by those skilled in the art using conventional dosage determination tests conducted with regard to the forgoing guidelines. Ranges provided herein are understood to be shorthand for all of the values within the range.

As used herein, the embodiments of this invention are defined to include pharmaceutically acceptable derivatives thereof. A "pharmaceutically acceptable derivative" means any pharmaceutically salt, ester, salt of an ester, or other derivative of a compound of this invention which, upon administration to a recipient, is capable of providing (directly or indirectly) a compound of this invention. Particularly favored derivatives are those that increase the bioavailability of the compounds of this invention when such compounds are administered to a mammal (e.g., by allowing an orally administered compound to be more readily absorbed into the blood, to increase serum stability or decrease clearance rate of the compound) or which enhance delivery of the parent compound to a biological compartment (e.g., the brain or lymphatic system) relative to the parent species. Derivatives include derivatives where a group which enhances aqueous solubility or active transport through the gut membrane is appended to the structure of formulae described herein.

The embodiments of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-napthalenesulfonate, nicotinate, nitrate, palmoate, phosphate, picrate, pivalate, propionate, salicylate, succinate, sulfate, tartrate, tosylate, and undeceneoate. Salts derived from appropriate bases include alkali metal (e.g., sodium), alkaline earth metal (e.g., magnesium), ammonium and N-(alkyl)4+ salts.

This invention also envisions the quaternization of any basic nitrogen-containing groups of the compounds disclosed herein. Water or oil-soluble or dispersible products may be obtained by such quaternization.

The embodiments of the invention can, for example, be administered by injection, intraocularly, intravitreally, subretinal, intravenously, intraarterially, subdermally, intramuscularly, or subcutaneously; or orally, buccally, nasally, transmucosally, directly to a diseased organ by catheter, topically, or in an ophthalmic preparation, with a dosage ranging from about 0.001 to about 100 mg/kg of body weight, or according to the requirements of the particular drug and more preferably from 0.5-10 mg/kg of body weight. It is understood that when a compound is delivered directly to the eye, considerations such as body weight have less bearing on the dose.

Frequency of dosing will depend on the agent administered, the progression of the disease or condition in the subject, and other considerations known to those of skill in the art. For example, pharmacokinetic and pharmacodynamics considerations for compositions delivered to the eye, or even compartments within the eye, are different, e.g., clearance in the subretinal space is very low. Therefore, dosing can be as infrequent as once a month, once every three months, once every six months, once a year, once every five years, or less. If systemic administration of antioxidants is to be performed in conjunction with administration of expression constructs to the subretinal space, it is expected that the dosing frequency of the antioxidant will be higher than the expression construct, e.g., one or more times daily, one or more times weekly.

Dosing may be determined in conjunction with monitoring of one or more signs or symptoms of the disease, e.g., visual acuity, visual field, night visions, etc. The amount of active ingredient that may be combined with the carrier materials to produce a single dosage form will vary depending upon the host treated and the particular mode of administration. A typical preparation will contain from about 1% to about 95% active compound (w/w). Alternatively, such preparations contain from about 20% to about 80% active compound. Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity ad course of the disease, condition or symptoms, the patient's disposition to the disease, condition or symptoms and the judgment of the treating physician.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, TWEEN® 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as TWEENs® or SPAN® and/or other similar emulsifying agents or bioavailability enhancers which are commonly used in the manufacture of pharmaceutically acceptable solid, liquid, or other dosage forms may also be used for the purposes of formulation.

In one or more embodiments, NACA or diNACA is administered in daily doses of about 0.5 to 150 mg/Kg. In other embodiments, NACA or diNACA is administered two or three times daily. In another aspect, NACA or diNACA is administered with a second active agent selected from ascorbic acid, cysteine hydrochloride, sodium bisulfate, sodium metabisulfite, sodium sulfite and the like; oil soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

In some embodiments, the dose of NACA or diNACA for administration is, 100, 150, 150, 300, 333, 400, 500, 600, 700, 750, 800, 900, 1,000, 2,500, 5,000, 7,500, or 10,000 mg per dose. In another aspect, the dose for administration is 0.001-0.01, 0.01-0.1, 0.1-0.25, 0.1-0.4, 0.35-0.5, 0.5-1, 102, 1-3, 1-4, 1-5, 1-2.5, 2.5-3.5, 4-6, 5-8, 6-9, 7-10 grams per dose.

In another aspect, NACA or diNACA is delivered orally via a mini-tablet, capsule, tablet, effervescent, dual release, mixed release, sachet, powder, or liquid. In another aspect, NACA or diNACA is administered prophylactically to prevent or reduce corneal endothelial cell loss. In another embodiment, the present invention includes a method for the treatment of corneal endothelial cell loss comprising: identifying a human in need of treatment for corneal endothelial cell loss; and administering to the human a therapeutically effective amount of NACA or diNACA sufficient to prevent or reduce corneal endothelial cell loss. It will be understood that, as with the other embodiments defined above, NACA or diNACA is administered in daily doses of about 0.5 to 150 mg/Kg. In another aspect, NACA or diNACA is administered two or three times daily. In another aspect, NACA or diNACA is administered with a second active agent as disclosed above.

In another aspect, the dose of NACA or diNACA for administration is 100, 150, 150, 300, 333, 400, 500, 600, 700, 750, 800, 900, 1,000, 2,500, 5,000, 7,500, or 10,000 mg per dose. In another aspect, the dose for administration is 0.001-0.01, 0.01-0.1, 0.1-0.25, 0.1-0.4, 0.35-0.5, 0.5-1, 102, 1-3, 1-4, 1-5, 1-2.5, 2.5-3.5, 4-6, 5-8, 6-9, 7-10 grams per dose.

In another aspect, the NACA is delivered orally via a mini-tablet, capsule, tablet, effervescent, dual release, mixed release, sachet, powder, or liquid. In another aspect, NACA or diNACA is administered prophylactically to prevent or reduce corneal endothelial cell loss.

As used herein, "susceptible to" or "prone to" or "predisposed to" a specific disease or condition or the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200% or more.

In another aspect, the method for the prevention of corneal endothelial cell loss in a human subject comprises, consists essentially or, of consists of: identifying a human patient in need of treatment for corneal endothelial cell loss; and administering to the human patient a therapeutically effective amount of N-acetylcysteine amide (NACA) or (2R,2R')-3,3-disulfanediyl bis(2-acetamidopropanamide) (diNACA) sufficient to prevent or reduce the corneal endothelial cell loss.

A method for the prevention or reduction of corneal endothelial cell loss in a human subject comprises, consists essentially or, of consists of: identifying a human in need of treatment for corneal endothelial cell loss; and administering to the human a therapeutically effective amount of N-acetylcysteine amide (NACA) or (2R,2R')-3,3'-disulfanediyl bis(2-acetamidopropanamide) (diNACA) sufficient to prevent or reduce the corneal endothelial cell loss.

Clinical Trial of NACA and/or DiNACA

A clinical trial can be conducted to demonstrate the ability of administered NACA and, separately, diNACA, to treat presbyopia, AIDS, antivenom, beta-thalassemia, cataract, chronic obstructive pulmonary disease, corneal endothelial cell loss, diabetes and diabetes-induced ulcers, macular degeneration, contrast-induced nephropathy, asthma, lung contusion, macular degeneration, methamphetamine-induced oxidative stress, multiple sclerosis, Parkinson's disease, platelet apoptosis, presbyopia, Tardive dyskinesia, Alzheimer disease, HIV, HIV-1-associated dementia, mitochondrial diseases, myocardial myopathy, neurodegenerative diseases, pulmonary fibrosis, retinitis pigmentosa, Usher syndrome, Stargardt syndrome, age-related macular degeneration, skin pigmentation, skin in need of rejuvenation, antimicrobial infection, and/or Friedreich's ataxia. An appropriate model system for the AIDS, antivenom, beta-thallassemia, cataract, chronic obstructive pulmonary disease, corneal endothelial cell loss, diabetes and diabetes-induced ulcers, macular degeneration, contrast-induced nephropathy, asthma, lung contusion, macular degeneration, methamphetamine-induced oxidative stress, multiple sclerosis, Parkinson's disease, platelet apoptosis, presbyopia, Tardive dyskinesia, Alzheimer disease, HIV, HIV-1-associated dementia, mitochondrial diseases, myocardial myopathy, neurodegenerative diseases, pulmonary fibrosis, retinitis pigmentosa, Usher syndrome, Stargardt syndrome, age-related macular degeneration, skin pigmentation, skin in need of rejuvenation, antimicrobial infection, and/or Friedreich's ataxia is selected and the diNACA, NAC, NACA, or combinations thereof can be provided separately, or together, and are comparted to a placebo control.

For example, one model would be similar to that used for demonstration of anti-presbyopic activity of EV06 (www.eyeworld.org/has-presbyopia-found-encore). For presbyopia, for each drug, the clinical study will be a prospective, randomized, double-masked, placebo-controlled study at one or more clinical sites including approximately 75 patients (45-55 years) with hyperopia, myopia, or emmetropia and a diagnosis of presbyopia. Patients will likely be randomized 2:1 (e.g., active=50:placebo=25). The investigational product will be given for 90 days and patients monitored during a 3-month follow-up period. At baseline, study patients will have DCNVA monitored as well as at visits to follow. Safety will be based on a comparison of adverse effects of active versus placebo arms. Efficacy will be based on a comparison of visual acuity measurements as measured by log MAR change in the bilateral vision of active versus placebo arms.

Similarly, trials can be conducted for the various conditions or diseases of oxidative stress selected from presbyopia, AIDS, antivenom, beta-thalassemia, cataract, chronic obstructive pulmonary disease, corneal endothelial cell loss, diabetes and diabetes-induced ulcers, macular degeneration, contrast-induced nephropathy, asthma, lung contusion, macular degeneration, methamphetamine-induced oxidative stress, multiple sclerosis, Parkinson's disease, platelet apoptosis, presbyopia, Tardive dyskinesia, Alzheimer disease, HIV, HIV-1-associated dementia, mitochondrial diseases, myocardial myopathy, neurodegenerative diseases, pulmonary fibrosis, retinitis pigmentosa, Usher syndrome, Stargardt syndrome, age-related macular degeneration, skin pigmentation, skin in need of rejuvenation, antimicrobial infection, and/or Friedreich's ataxia, It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains.

All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" issued to indicate the presence of the recited integer (e.g., a feature, an element, a characteristic, a property, a method/process step or a limitation) or group of integers (e.g., feature(s), element(s), characteristic (s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refer condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least 1, 2, 3, 4, 5, 6, 7, 10, 12 or 15%.

Additionally, the section headings herein are provided for consistency with the suggestions under 37 CFR 1.77 or otherwise to provide organization cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention (s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for using diNACA as a prodrug to deliver diNACA, NACA or NAC to treat diseases or disorders of oxidative stress in a mammal consisting of ocularly administering topically, intraocularly, intrahumorally, subretinally, intravitreally, or by implantation a therapeutically effective amount of a composition consisting of diNACA and a pharmaceutically acceptable carrier to the mammal to treat corneal endothelial cell loss, Stargardt syndrome, or age-related macular degeneration, wherein the diNACA is administered in daily doses of about 0.01 to 150 mg/Kg, and wherein diNACA and NACA are detectable in vitreous humor 7 days after administration.

2. The method of claim 1, wherein the diNACA is administered as eye drops, insert, injection, or implant.

3. A method for treating corneal endothelial cell loss in a human subject consisting of:

identifying a human patient in need of treatment for corneal endothelial cell loss; and ocularly administering to the human patient topically, intraocularly, intrahumorally, subretinally, intravitreally, or by implantation a therapeutically effective amount of (2R,2R')-3,3'-disulfanediyl bis(2-acetamidopropanamide) (diNACA) sufficient to reduce the corneal endothelial cell loss, wherein the diNACA is administered in daily doses of about 0.01 to 150 mg/Kg, and wherein the amount is sufficient to be detectable in the vitreous humor as diNACA and NACA in the eye 7 days after administration.

4. The method of claim 3, wherein diNACA is provided in or with a pharmaceutically acceptable carrier which can be eye drops, insert or implant.

5. The method of claim 3, wherein the corneal cell loss is due to ophthalmic surgery and the composition is provided to the subject after ophthalmic surgery.

6. The method of claim 3, wherein the diNACA is administered in daily doses of about 0.8 mg per eye.

7. The method of claim 3, wherein the diNACA is administered two or three times daily.

8. The method of claim 3, wherein the diNACA is administered with a second active agent selected from at least one of ascorbic acid, cysteine hydrochloride, sodium bisulfate, sodium metabisulfite, sodium sulfite, ascorbyl palmitate, butylated hydroxyanisole (BHA), butylated hydroxytoluene (BHT), lecithin, propyl gallate, α-tocopherol, citric acid, ethylenediamine tetraacetic acid (EDTA), sorbitol, tartaric acid, or phosphoric acid.

9. The method of claim 3, wherein the dose of diNACA for administration is about 100, 150, 150, 300, 333, 400, 500, 600, 700, 750, 800, 900, 1,000, 2,500, 5,000, 7,500, or 10,000 mg per dose.

10. The method of claim 3, wherein the diNACA is delivered orally via a mini-tablet, capsule, tablet, effervescent, dual release, mixed release, sachet, powder, ocular insert, ocular implant, eye drop or liquid.

11. The method of claim 3, wherein the diNACA is administered prophylactically, post-surgically or after other procedures or treatments, to reduce corneal endothelial cell loss.

* * * * *